US006899864B2

(12) United States Patent
Hnatowich et al.

(10) Patent No.: US 6,899,864 B2
(45) Date of Patent: May 31, 2005

(54) MORPHOLINO IMAGING AND THERAPY

(75) Inventors: Donald J. Hnatowich, Brookline, MA (US); Mary Rusckowski, Southborough, MA (US); Guozheng Liu, Worcester, MA (US)

(73) Assignee: Immunomedics, Inc., Morris Plains, NJ (US)

(*) Notice: Subject to any disclaimer, the term of this patent is extended or adjusted under 35 U.S.C. 154(b) by 132 days.

(21) Appl. No.: 10/112,094

(22) Filed: Apr. 1, 2002

(65) Prior Publication Data

US 2003/0003102 A1 Jan. 2, 2003

Related U.S. Application Data

(60) Provisional application No. 60/279,809, filed on Mar. 30, 2001, now abandoned, and provisional application No. 60/341,794, filed on Dec. 21, 2001.

(51) Int. Cl.$^7$ ........................ A61K 51/00; A61K 3/535; A61B 5/055
(52) U.S. Cl. .................... 424/1.65; 424/1.69; 424/1.77; 424/9.3; 424/9.36; 424/9.6; 514/231.8
(58) Field of Search ............................... 424/1.65, 1.69, 424/1.77, 178.1, 280.1, 9.3, 9.341, 9.36, 9.6; 514/231.8; 536/22.1, 24.1, 24.2, 24.3, 24.31, 25.32, 26.6

(56) References Cited

U.S. PATENT DOCUMENTS

| | | | |
|---|---|---|---|
| 3,927,193 A | 12/1975 | Hansen et al. | |
| 4,331,647 A | 5/1982 | Goldenberg | |
| 4,348,376 A | 9/1982 | Goldenberg | |
| 4,361,544 A | 11/1982 | Goldenberg | |
| 4,444,744 A | 4/1984 | Goldenberg | |
| 4,460,459 A | 7/1984 | Shaw et al. | |
| 4,460,561 A | 7/1984 | Goldenberg | |
| 4,468,457 A | 8/1984 | Goldenberg et al. | |
| 4,474,893 A | 10/1984 | Reading | |
| 4,479,895 A | 10/1984 | Auditore-Hargreaves | |
| 4,624,846 A | 11/1986 | Goldenberg | |
| 4,782,840 A | 11/1988 | Martin, Jr. et al. | |
| 4,818,709 A | 4/1989 | Primus et al. | |
| 4,863,713 A | 9/1989 | Goldwin et al. | |
| 4,932,412 A | 6/1990 | Goldenberg | |
| 4,946,778 A | 8/1990 | Ladner et al. | |
| 5,142,047 A | 8/1992 | Summerton et al. | |
| 5,185,444 A | 2/1993 | Summerton et al. | |
| 5,482,698 A | * 1/1996 | Griffiths | .................... 424/1.41 |
| 5,645,985 A | 7/1997 | Froehler et al. | |
| 5,698,685 A | 12/1997 | Summerton et al. | |
| 5,716,595 A | 2/1998 | Goldenberg | |
| 5,874,540 A | 2/1999 | Hansen et al. | |
| 5,958,408 A | 9/1999 | Griffiths et al. | |
| 6,331,175 B1 | 12/2001 | Goldenberg | |

OTHER PUBLICATIONS

Barbet, J. et el., "Pretargeting with the Affinity Enhancement System for Radioimmunotherapy", *Cancer Biootheraphy & Radiopharmaceuticals*:vol. 14; No. 3:153–166 (1999).

Childs, R. L. et al., "Optimum Conditions for Labeling of DTPA–Coupled Antibodies with Technetium–99m," *J. Nuc. Med.*; vol. 26; No. 3:293–299 (1985).

Crooke, R.M. et al., "Metabolism of Antisense Oligonucleotides in Rat Liver Homogenates," *J. Pharmacology and Experimental Therapeutics*: vol. 292; No. 1:140.149 (2000).

Gautherot, E. et al., "Pretargeted Radioimmunotherapy of Human Colorectal Xenografts with Bispecific antibody and $^{131}$I–Labeled bivalent Hapten," *Journal of Nuclear Medicne*: vol. 41; No. 3:480–487 (2000).

Gestin, J.F. et al., "Two–Step Targeting of Xenografted colon Carcinoma Using a Bispecific Antibody and $^{188}$Re–Labeled Bivalent Hapten: Biodistribution and Dosimetry Studies," *Journal of Nuclear Medicine*: vol. 42; No. 1:146–153 (2001).

Goodwin el al., "Pre–Targeted immunoscintigraphy of Murine Tumors with Indium–111–Labeled Bifunctional Haptens," *Journal of Nuclear Medicine*: vol. 29, No. 1:226–234 (1988).

Hansen et al., "Characterization of Second–Generation Monocolonal Antibodies Against Carcinoembryonic Antigen," *Cancer*: vol. 71, No. 11:3478–3485 (1993).

Hnatowich et al., "Investigations of Avidin and Biotin for Imaging Applications," *Journal of Nuclear Medicine*: vol. 28, No. 8:1294–1302 (1987).

Hnatowich, D.J., "antisense and Nuclear Medicine," *Journal of Nuclear Medicine*: vol. 40, No. 4:693–703 (1999).

Kalofonos et al., "Imaging of Tumor in Patients with Indium–111–Labeled Biotin and Streptavidin– Conjugated Antibodies: Preliminary Communication," *Journal of Nuclear Medicine*: vol. 31:1791–1796 (1990).

Karacay. H. et al., "Experimental Pretargeting Studies of Cancer with a Humanized anti–CEA x Murine anti–[ln–DTPA] Bispecific Antibody Construct and a $^{99m}$Tc–/$^{188}$Re–Labeled Peptide," *Bioconjugate Chem.*, vol. 11, No. 6: 842–854 (2000).

(Continued)

*Primary Examiner*—Michael G. Hartley
(74) *Attorney, Agent, or Firm*—Heller Ehrman White and McAuliffe LLP

(57) ABSTRACT

The present invention provides a kit and a method for targeting of a diagnostic or therapeutic agent to a target site in a mammal having a pathological condition. The kit comprises, in separate containers, (a) a first conjugate comprising a targeting moiety and a Morpholino oligomer, wherein the targeting moiety selectively binds to a primary, target-specific binding site of the target site or to a substance produced by or associated with the target site; (b) optionally, a clearing agent; and (c) a second conjugate comprising a complementary Morpholino oligomer and a diagnostic agent or therapeutic agent. The method comprises administering (a), optionally (b), and (c) to a mammal.

47 Claims, 9 Drawing Sheets

OTHER PUBLICATIONS

Kaukinen, U. et al., "The reactivity of phosphodiester bonds within linear single-stranded oligoribonucleotides is strongly dependent on the base sequence," *Nucleic Acids Research*: vol. 30; No. 2:468–474 (2002).

Kllbanov et al., "Blood Clearance of Radiolabeled Antibody: Enhancement by Lactosamination and Treatment with Biotin–Avidin or Anti–Mouse," *Journal of Nuclear Medicine*: vol. 29, No. 12:1951–1956 (1988).

Liu G. et al., "Tumor Pretargeting in Mice Using $^{99m}Tc-La$-beled Morpholino, a DNA Analog," *Journal Nuclear Medicine*: vol. 43, No. 3:384–391 (2002).

Lubic, S.P. et al., "Biodistribution and Dosimetry of Pretargeted Monoclonal Antibody 2D12.5 and Y–Janus–DOTA in BALB/c Mice with KHJJ Mouse Adenocarcinoma," *Journal Nuclear Medicine*: vol. 42, No. 4:670–678 (2001).

Mang'era, K., et al., "Initial Investigations of $^{99m}$Tc–labeled morpholinos for radiopharmaceutical applications," *European Journal of Nuclear Medicine*: vol. 28, No. 11:1682–1689 (2001).

Mardirossian, G. et al., "In Vivo Hybridization of Technetium–99m–Labeled Peptide Nucleic Acid (PNA)," *Journal of Nuclear Medicine*: vol. 38; No. 6:907–913 (1997).

Milstein et al., "Hybrid hybridomas and the production of bi–specific monoclonal antibodies," *Immunology Today*: vol. 5, No. 10:299–304 (1984).

Morassutti, C. et al., "Effect of Oligomer Length and Base Substitutions on the Cytotoxic Activity and Specific Nuclear Protein Recognition of GTn Oligonucleotides in the Human Leukemic CCRF–CEM Cell Line," *Nucleosides & Nucleotides*; vol. 18:1711–1716 (1999).

Oehr et al., "Streptavidin and Biotin as Potential Tumor Imaging," *Journal of Nuclear Medicine*: vol. 29, No. 5:728–729 (1988).

Paganelli et al., "Three–Step Monoclonal Antibody tumar Targeting in Carcinoembryonic Antigen–positive Patients," *Cancer Research*: vol. 51:5960–5966 (1991).

Paganelli et al., "Monoclonal Antibody pretargetting Techniques for Tumour Localization: the Avidin–biotin System," *Nuclear Medicine Communication*: vol. 12:211–234 (1991).

Rusckowski et al., "Pretargeting Using Peptide Nucleic Acid," *Cancer*: vol. 80, No. 12:2699–2705 (1997).

Schechter et al., "Indirect Immunotargeting of CIS–PT to Human Epidermoid Carcinoma KB Using the Avidin–Biotin System." *Int. J. Cancer*: vol. 48:167–172 (1991).

Shafer, R.H. et al., "Biological Aspects of DNA/RNA Quadruplexes," *Biopoly (Nucleic Acid Sci.)*: vol. 56:209–227 (2001).

Sinitsyn et al., "Rapid Blood clearance of Biotinylated IgG After Infusion of Avidin," *Journal of Nuclear Medicine*: vol. 30, No. 1:66–69 (1989).

Stickney et al., "Bifunctional Antibody: A binary Radiopharmaceutical Delivery System for Imaging Colorectal Carcinoma," *Cancer Research*: vol. 51:6650–6655 (1991).

Summerton et al., Review Article: Morpholino antisense Oligomers: Design, Preparation, and Properties, *Antisense Nucleic Acid Drug Development*: vol. 7:187–195 (1997).

Wang, G. et al., "Defining the Peptide Nucleic Acids (PNA) Length Requirement for PNA Binding–Induced Transcription and Gene Expression," *Journal Molecular Biology*: vol. 313:933–940 (2001).

Wang, Y. et al. "Pretargeting with Amplification Using Polymeric Peptide Nucleic Acid," *Bioconjugate Chem.*: vol. 12:807–816 (2001).

Winnard, P. et al., "Preparation and Use of NHS–MAG$_3$ for Technetium–99m Labeling of DNA," *Nuclear Medicine & Biology*: vol. 24:425–432 (1997).

Yuan et al., "Pharmacokinetic Analysis of Two–Step Approaches Using Bifunctional and Enzyme– Conjugated Antibodies1," *Cancer Research*: vol. 51:3119–3130 (1991).

Zhang, Y.M. et al., "Influence of Different Chelators (HYNIC, MAG3 and DTPA) on Tumor Cell Accumulation and Mouse Biodistribution of Technetium–99m Labeled to Antisense DNA," *European Journal of Nuclear Medicine*: vol. 27:1700–1707 (2000).

Zhao, Q. et al., "Pattern and Kinetics of Cytokine Production Following Administration of Phosphorothioate Oligonucleotides in Mice," *Antisense & Nucleic Acid Drug Development*: vol. 7:495–502 (1997).

Zhu, H. et al., "Tumor Pretargeting for Radioimmunodetection and Radioimmunotherapy," *Journal of Nuclear Medicine*: vol. 39:65–76 (1998).

* cited by examiner

MORPHOLINO IMAGING AND THERAPY

CROSS-REFERENCE TO RELATED APPLICATIONS

This application is based on U.S. provisional patent application Ser. No. 60/279,809, filed Mar. 30, 2001 now abandoned, and 60/341,794, filed Dec. 21, 2001. The entire contents of these applications, including their specifications, claims and drawings, are incorporated herein by reference in their entirety.

FIELD OF THE INVENTION

The present invention is directed to a kit for targeting of a diagnostic or therapeutic agent to a target site in a mammal, as well as to a method for diagnosing or treating a pathological condition in a multistep process using a kit containing a complementary pair of single-stranded Morpholino oligomers.

BACKGROUND OF THE INVENTION

The objective of drug targeting research is to improve the effectiveness of therapeutic drugs by delivering them directly to the targeted tumor sites and allowing a more effective dosing at these sites, thereby reducing non-tumor-related side effects. Another objective is to achieve an absolute accretion of the therapeutic agent at the target site thereby increasing the target/non-target ratio.

Different targeting vectors comprising diagnostic or therapeutic agents conjugated to a targeting moiety for selective localization have long been known. Examples of targeting vectors include diagnostic agent or therapeutic agent conjugates of targeting moieties such as antibodies or antibody fragments, cell- or tissue-specific peptides, hormones and other receptor binding molecules. For examples, antibodies against different determinants associated with pathological and normal cells, as well as associated with pathogenic microorganisms, have been used for the detection and treatment of a wide variety of pathological conditions or lesions. In these methods, the targeting antibody is directly conjugated to an appropriate detecting or therapeutic agent as described, for example in, Hansen et al., U.S. Pat. No. 3,927,193 and Goldenberg, U.S. Pat. Nos. 4,331,647, 4,348, 376, 4,361,544, 4,468,457, 4,444,744, 4,460,459, 4,460,561, 4,624,846 and 4,818,709, the disclosures of all of which are incorporated herein by reference.

One of the problems encountered in direct targeting methods is that a relatively small fraction of the conjugate actually binds to the target site, while the majority of the conjugate remains in circulation and compromises in one way or another the function of the targeted conjugate. Other problems include high background and low resolution when a diagnostic agent is administered and marrow toxicity or systemic side effects when a therapeutic agent is attached to a long circulating targeting moiety.

Pretargeting methods have been developed to increase the target:background ratios of the detection or therapeutic agents. Examples of pretargeting and biotin/avidin approaches are described, for example, in Goodwin et al., U.S. Pat. No. 4,863,713; Goodwin et al., J. Nucl. Med. 29:226 (1988); Hnatowich et al., J. Nucl. Med. 28:1294 (1987); Oehr et al., J Nucl. Med. 29:728 (1988); Klibanov et al., J. Nucl. Med. 29:1951 (1988); Sinitsyn et al., J. Nucl. Med. 30:66 (1989); Kalofonos et al., J. Nucl. Med. 31:1791 (1990); Schechter et al., Int. J. Cancer. 48:167 (1991); Paganelli et al., Cancer Res. 51:5960 (1991); Paganelli et al., Nucl. Med. Commun. 12:211 (1991); Stickney et al., Cancer Res. 51:6650 (1991); and Yuan et al., Cancer Res. 51:3119 (1991); all of which are incorporated by reference herein in their entireties.

In pretargeting methods, a primary targeting species (which is not bound to a diagnostic agent or therapeutic agent) comprising a first targeting moiety which binds to the targeting site and a binding site that is available for binding by a subsequently administered second targeting species is targeted to an in vivo target site. Once sufficient accretion of the primary targeting species is accomplished, a second targeting species comprising a diagnostic or therapeutic agent and a second targeting moiety, which recognizes the available binding site of the primary targeting species, is administered.

An illustrative example of pretargeting methodology is the use of a biotin-(strept)avidin system to administer a cytotoxic radioantibody to a tumor. In the first step, a monoclonal antibody targeted against a tumor-associated antigen is conjugated to avidin (or biotin) and administered to a patient who has a tumor recognized by the antibody. In the second step, the therapeutic agent, via its attached biotin (or avidin), is taken up by the antibody-avidin (or -biotin) conjugate pretargeted to the tumor.

However, difficulties have arisen in the applications of biotin-avidin or (strept)avidin system during pretargeting. First of all, unless properly constructed, radiolabeled biotins may be subject to plasma biotinidase degradation. Furthermore, when conjugated to antibodies, strept/avidin and avidin can generate anti-strept/avidin antibodies in a patient. Finally, the potential effects of endogenous biotin during in vivo pretargeting can lead to the disappearance of biotin binding expression because of saturation by biotin. This happened, for example, when one strept/avidin-conjugated antibody localized in a nude mouse xenograft became saturated with biotin. Rusckowski et al., Cancer 80:2699–705 (1997). A three-step strategy involving administration of biotinylated monoclonal antibody, avidin, followed by radiolabeled biotin alleviates some of the drawbacks; however, this procedure is considered complex for imaging and does not address immunogenecity.

Another recognized example of pretargeting method involves the use of the bispecific antibody-hapten recognition system which uses a radiolabeled hapten and a bispecific antibody in place of (strept)avidin and biotin. Barbet, J. et al. Cancer Biother. Radiopharm. 14:153–166 (1999); Karacay, H. et al., Bioconj. Chem. 11: 842–854 (2000); Gautherot, E. et al., J. Nucl. Med. 41:480–487 (2000); Lubic, S. P. et al., J. Nucl. Med. 42:670–678 (2001); Gestin, J. F. et al., J. Nucl. Med. 42:146–153 (2001). The hapten is often a coordination complex, for example, indium-DTPA. The bispecific antibody is the product of linking two antibodies or antibody fragments against separate determinants, the hapten and a tumor marker such as carcinoembryonic antigen. In addition to the need to prepare bispecific antibodies, this approach may suffer from lower affinities. The affinity of an antibody for its hapten, particularly for a monovalent one, is orders of magnitude lower than that of (strept)avidin for biotin. Mathematical modeling has shown that a high affinity between an antibody and its hapten is an important determinant of successful pretargeting. Zhu, H. et al., J. Nucl. Med. 39:65–76 (1998).

As an alternative to the biotin-avidin and bispecific antibody-hapten systems for pretargeting, single-stranded oligomers, such as peptide nucleic acid (PNA), have been used. Single-stranded oligomers bind specifically to their complementary single-stranded oligomers by in vivo hybridization. A single-stranded PNA bound to a targeting moiety is first administered to a patient, followed by the single-stranded complementary PNA radiolabeled with a diagnostic agent. An example of this methodology is described in Rusckowski et al., *Cancer* 80:2699–705 (1997). An optional intermediate step can be added to the two-step method by administration of a clearing agent. The purpose of the clearing agent is to remove circulating primary conjugate which is not bound at the target site. This is disclosed by Griffiths et al., in U.S. Pat. No. 5,958,408, which is incorporated herein by reference.

Chemical modifications to the backbone of these single-stranded oligomers for attachment to radionucleotides are usually required to improve nuclease stability and decrease protein binding affinities. The influence of three distinct chemical modifications to one 18 mer phosphorothioate DNA to permit labeling with $^{99m}$Tc have been compared in vitro and in vivo in mice. Zhang, Y. M. et al., *Eur. J. Nucl. Med.* 27:1700–1707 (2000). While the association rate constant for hybridization was found to be independent of labeling method, both cellular accumulations in culture and the pharmacokinetic behavior of the radiolabel in normal mice was strongly influenced by the labeling method.

These in vivo properties of oligomers may possibly be influenced by changes in their chain length and/or base sequences. Conceivably, the pharmacokinetics of an oligomer may thereby be modified in a useful manner if the influences of chain length and base sequence were to be understood. Despite this possibility (and as in the case of the chemical modifications), these additional influences have almost entirely gone uninvestigated thus far. In part, this may be attributed to constraints placed on these parameters by the application. For example, antisense chemotherapy is thought to achieve efficacy usually by the hybridization of a short, single-chain oligomer with a base sequence complementary to that of its mRNA target. Hnatowich, D. J., *J. Nucl. Med.* 40:693–703 (1999). The base sequence, and to an extent the chain length as well, are thus restricted to those providing the desired hybridization. Nevertheless, there are combinations of bases that have received attention. One example is the presence of a G-quartet (i.e. four guanine bases in a row) in either phosphodiester or phosphorothioate DNAs. Shafter, R. H. et al., *Biopoly (Nucleic Acid Sci.)* 56:209–227 (2001). In the case of these chemical forms of DNAs at least, the stacking of the guanine bases provides the oligonucleotides with a particular three dimensional quadruplex structure. This structure is apparently responsible for a variety of sequence-specific effects with significance to various biological processes. Shafter, R. H. et al., *Biopoly. (Nucleic Acid Sci)* 56:209–227 (2001). Another example is the CpG motif, a cytosine base followed immediately by a guanine, that has been shown to be immunostimulatory. Zhao, Q. et al., *Antisense Nucleic Acid Drug Dev.* 7:495–502 (1997). The influences of these sequences, if any, on pharmacokinetics has yet to be established.

A variety of other published reports have appeared concerning the in vitro influences of oligomer chain length and sequence. Cytotoxicity in one cell line of phosphodiester DNAs composed entirely of guanine and thymidine bases was found to require at least a chain length of 20 bases and the cytotoxicity disappeared with the introduction of adenines or cytosines at either end. Morassutti, C. et al., *Nucleosides & Nucleotides* 18:1711–1716 (1999). The efficiency with which PNAs initiated transcription and gene expression in cells was found to be optimum at chain lengths of 16 to 18 bases. Wang, G. et al., *J. Mol. Biol.* 313:933–940 (2001). Rat liver homogenates have been used ex vivo to investigate the metabolism of a series of phosphorothioate DNAs differing in chain length and base sequence. Crooke, R. M. et al., *J. Pharm. Exp. Therapeutics* 292:140–149 (2000). All oligomers were degraded primarily by 3 ' exonucleases with the rate of metabolism increasing with increasing chain length. The rate and extent of nuclease metabolism was also related to base sequence in that pyrimidine-rich oligonucleotides were more labile. This particular investigation was unusual in that the influence of sterioisomerism was also studied. The metabolism rate was found to be more rapid for one of the diasterioisomers than the other with mixtures being digested at rates in between. Finally, a recent report described the influence of base sequence on reactivity of the phosphodiester bond in RNAs. Kaukinen, U. et al., *Nucl. Acids Res.* 30:468–474 (2002).

Despite the several advantages over the strept/avidin-biotin and bispecific antibody-hapten systems, a few limitations exist in the use of these oligomers in pretargeting. These limitations include poor specificity, possible insolubility in aqueous solutions, and high costs.

A need continues to exist for an improved kit and method for in vivo targeting to deliver a therapeutic or diagnostic agent to a target site in a mammal, that is more specific, affordable and inexpensive and provides higher target uptake and lower uptake in normal tissues.

SUMMARY OF THE INVENTION

Accordingly, an object of the present invention is to provide a kit and a method useful for targeting of a diagnostic or therapeutic agent in a mammal which can be prepared from relatively inexpensive starting materials but yet provides better specificity, stability, predictable targeting and/or more desirable antigen-antibody effects than conventional and other known kits and methods.

It is another object to provide an alternative method useful for tumor localization/imaging by stepwise targeting using a pair of single-stranded Morpholino oligomers (MORFs, as defined below) instead of strep/avidin-biotin, peptide nucleic acids and other oligomers, wherein a radiolabeled targeting moiety is highly accreted to the primary target-specific binding site within the target thereby providing a good tumor to non-tumor ratio for imaging purposes.

These and other objects are achieved, in accordance with one embodiment of the present invention by the provision of a kit for targeting of a diagnostic or therapeutic agent in a mammal comprising: (A) a first conjugate comprising a targeting moiety and a Morpholino oligomer, wherein said targeting moiety selectively binds to a primary, target-specific binding site of the target site or to a substance produced by or associated with the target site; (B) optionally, a clearing agent; and (C) a second conjugate comprising a complementary Morpholino oligomer and a diagnostic agent or therapeutic agent.

The targeting moiety of step (a) preferably comprises an antibody, especially a humanized antibody or an antigen-binding fragment of a humanized antibody. One such humanized antibody is an anti-carcinoembryonic antigen (CEA) antibody. The targeting moiety is selected from the group consisting of proteins, small peptides, polypeptides, enzymes, hormones, steroids, cytokines, neurotransmitters, oligomers, vitamins and receptor binding molecules.

In accordance with another aspect of the present invention, a kit is provided, as described above, wherein the length of the Morpholino oligomer and its complementary Morpholino oligomer is at least about 6 bases to about 100 bases. In addition, the Morpholino and its complementary Morpholino oligomer can be a 15-mer, an 18-mer or a 25-mer. The target moiety is bound to a 15-mer, an 18-mer or a 25-mer Morpholino oligomer.

In a preferred embodiment, the clearing agent is an anti-idiotypic antibody or antigen-binding antibody fragment.

In another preferred embodiment, the therapeutic agent is selected from the group consisting of antibodies, antibody fragments, drugs, toxins, nucleases, hormones, immunomodulators, chelators, boron compounds, photoactive agents or dyes and radioinuclides.

In yet another preferred embodiment, the diagnostic agent is selected from the group consisting of radionuclides, dyes, contrast agents, fluorescent compounds or molecules and enhancing agents useful for magnetic resonance imaging (MRI).

The present invention contemplates an targeting method for delivering a diagnostic or therapeutic agent to a target site in a mammal, comprising: (a) administering to said mammal a first conjugate comprising a targeting moiety and a Morpholino oligomer, wherein said targeting moiety selectively binds to a primary, target-specific binding site of the target site or to a substance produced by or associated with the target site; (b) optionally, administering to said mammal a clearing agent, and allowing said clearing agent to clear non-localized first conjugate from circulation; and (c) administering to said mammal a second conjugate comprising a complementary Morpholino oligomer and a diagnostic agent or therapeutic agent, wherein said complementary Morpholino oligomer binds its Morpholino oligomer complement on the first conjugate thereby targeting the diagnostic or therapeutic agent to the target site.

Other objects, features and advantages of the present invention will become apparent from the following detailed description and appended claims.

DETAILED DESCRIPTION OF THE INVENTION

Figure 1A:
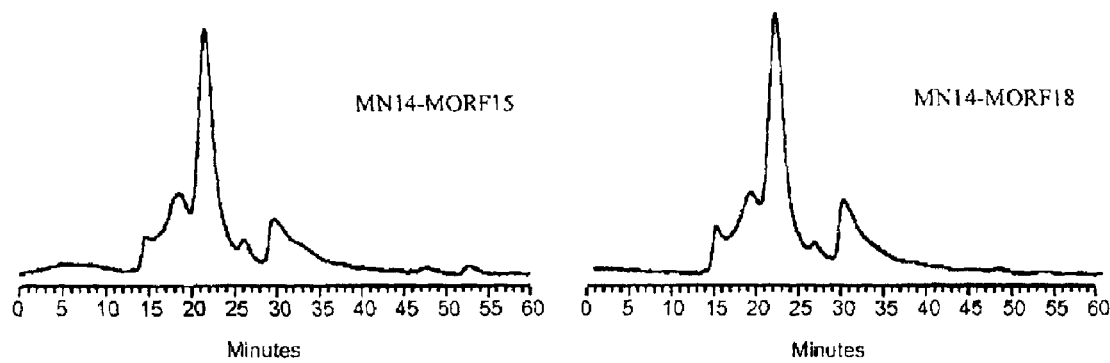
FIG. 1. A. UV absorption spectra of MORF15 (0.025 µg/µL) and native MN14 (0.5 µg/µL). B. Size exclusion HPLC UV chromatograms of MN14-MORF15 (left panel) and MN14-MORF18 (right panel) at 280 nm. C–D. Absorptions at 280 and 265 nm vs. weight of native MN14 (C) and native MORF15 (D).

Unless otherwise specified, "a" or "an" means "one or more".

The present invention provides a kit and a method useful for in vivo targeting of a diagnostic or therapeutic agent in a mammal (preferably human) comprising: (A) a first conjugate comprising a targeting moiety and a Morpholino oligomer, wherein said targeting moiety selectively binds to a primary, target-specific binding site of the target site or to a substance produced by or associated with the target site; (B) optionally, a clearing agent; and (C) a second conjugate comprising a complementary Morpholino oligomer and a diagnostic agent or therapeutic agent.

The targeting moiety may be, for example, an antibody or an antigen binding antibody fragment. Preferred are the monoclonal antibodies (Mabs) due to their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are also contemplated, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the invention include F(ab')$_2$, F(ab)$_2$, Fab', Fab, Fv and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This will include genetically-engineered or recombinant antibodies and proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is incorporated herein by reference.

Fab' fragments may be conveniently made by reductive cleavage of F(ab')$_2$ fragments, which themselves may be made by pepsin digestion of intact immunoglobulin, under reducing conditions, or by cleavage of F(ab')$_2$ fragments which result from careful papain digestion of whole immunoglobulin. The fragments may also be produced by genetic engineering.

It should be noted that mixtures of antibodies and immunoglobulin classes can be used, as can hybrid antibodies. Multispecific, including bispecific and hybrid, antibodies and antigen binding antibody fragments are useful in the methods of the present invention. Bispecific and hybrid antibodies are capable of specifically binding to at least one epitope on the marker substances, or on a component of the second conjugate. These antibodies preferably are comprised of at least two different substantially monospecific antibodies or antibody fragments, which at least bind to at least one epitope on the marker substance produced by or associated with the cancer cells and with at least one epitope of a component of the second conjugate. Multispecific antibodies and antibody fragments with dual specificities can be prepared analogously to the anti-tumor marker hybrids disclosed in U.S. Pat. No. 4,361,544, the contents of which are incorporated by reference herein in their entirety. Other techniques for preparing hybrid antibodies are disclosed in, for example, U.S. Pat. Nos. 4,474,893 and 4,479,895, and in Milstein et al., *Immunol. Today* 5:299, (1984), the contents of which are incorporated by reference herein in their entirety.

Also preferred are antibodies having a specific immunoreactivity to a marker substance produced by or associated with the cancer cells of at least 60% and a cross-reactivity to other antigens or non-targeted substances of less than 35%. A monoclonal antibody that specifically targets tumor sites by binding to antigens produced by or associated with the tumors is particularly preferred.

Antibodies against tumor antigens are known. For example, antibodies and antibody fragments which specifically bind markers produced by or associated with tumors have been disclosed, inter alia, in Hansen et al., U.S. Pat. No. 3,927,193, and Goldenberg's U.S. Pat. Nos. 4,331,647, 4,348,376, 4,361,544, 4,468,457, 4,444,744, 4,818,709 and 4,624,846, the contents of all of which are incorporated herein by reference in their entirety. In particular, antibodies against an antigen, e.g., a gastrointestinal, lung, breast, prostate, ovarian, testicular, brain or lymphatic tumor, a sarcoma or a melanoma, are advantageously used.

The antibodies and antigen-binding antibody fragments useful in the methods of the present invention may be conjugated to the member of the binding pair by a variety of methods of chemical conjugation known in the art. Many of these methods are disclosed in the above-referenced U.S. patents and patent applications. See also Childs et al., *J. Nuc. Med.* 26:293 (1985), the contents of all of which are incorporated herein by reference in their entirety.

One monoclonal antibody useful in the present invention is MN-14, a second generation CEA-antibody that has ten times more affinity for CEA than the first generation version, NP-4. Hansen et al., *Cancer* 71:3478–85, (1993). MN-14 internalizes slowly, making it suitable for targeting approach, and has been chimerized and humanized. Leung et al., U.S. Pat. No. 5,874,540.

Other targeting moieties useful in the present invention can also be non-antibody species selecting from the group consisting of proteins, small peptides, polypeptides, enzymes, hormones, steroids, cytokines, neurotransmitters, oligomers, vitamins, and receptor binding molecules, which preferentially bind marker substances that are produced by or associated with the target site.

Morpholino oligomers (herein "Morpholinos" or "MORFs") bind and inactivate selected RNA sequences. These oligomers are assembled from four different Morpholino subunits, each of which contains one of the four genetic bases (A, G, C, T or U), linked to a six-membered morpholine ring. These subunits, as 15–25 mers, are joined together in a specific order by non-ionic phosphorodiamidate intersubunit linkages to produce a Morpholino oligomer. They may offer better antisense properties than do DNA, RNA, and their analogs having five-membered ribose or deoxyribose backbone moieties joined by ionic linkages. Summerton's work on Morpholinos is disclosed in U.S. Pat. Nos. 5,142,047 and 5,185,444, the contents of which are herein incorporated by reference. Morpholinos are commercially available from Gene Tools, LLC., Corvallis, Oreg.

Because they are readily delivered to the target, Morpholinos are effective tools for genetic studies and drug target validation programs. They are completely resistant to nucleases. A more rigid MORF backbone may offer better access during duplex formation when compared with a peptide backbone or with the more common sugar backbone. When compared to PNAs, Morpholinos are less expensive and more soluble in aqueous solutions, and provide better predictable targeting and higher efficacy in RNA binding affinities.

In the present invention, a Morpholino oligomer (herein MORF) bound to a targeting antibody is in vivo hybridized to the complementary MORF (herein cMORF) bound to a diagnostic or therapeutic agent. In a preferred embodiment, the length of the MORF and its complementary Morpholino (cMORF) is from 6 bases to about 100 bases, for example, MORF15 and cMORF15 (15-mer), MORF18 and cMORF18 (18-mer) or MORF25 and cMORF25 (25-mer).

The MORFs used in the present invention include a 15-mer (5' equivalent TGT-ACG-TCA-CAA-CTA-linker-amine (herein MORF15), and TAG-TTG-TGA-CGT-ACA-linker-amine (herein complementary MORF15 or cMORF15)), an 18-mer (5' equivalent CGG-TGT-ACG-TCA-CAA-CTA-linker-amine (herein MORF 18) and TAG-TTG-TGA-CGT-ACA-CCC-linker-amine (herein complementary MORF18 or cMORF18)), and a 25-mer (5' equivalent T-GGT-GGT-GGG-TGT-ACG-TCA-CAA-CTA-linker-amine (herein MORF25), and TAG-TTG-TGA-CGT-ACA-CCC-ACC-ACC-A-linker-amine (herein complementary MORF25 or cMORF25)).

The Morpholino oligo structure (Summerton and Weller, *Antisense Nucl. Acid Drug Dev.* 7:187–95, 1997) used in the present invention, is shown below as:

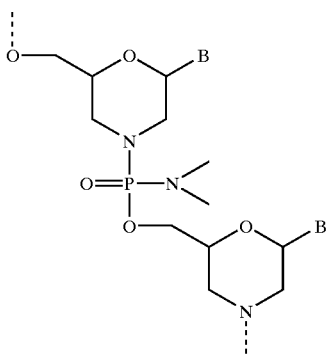

B=adenine, cytosine, guanine. thymine/uracil

Clearing agents known in the art may be used in accordance with the present invention. For example, if the first conjugate comprises avidin or streptavidin, biotin may be used as a clearing agent. Alternatively, if the first conjugate comprises biotin, avidin or streptavidin may be used as a clearing agent.

In a preferred embodiment, the clearing agent is an antibody which binds the binding site of the targeting moiety, wherein the targeting moiety can be an antibody, an antigen-binding antibody fragment or a non-antibody targeting moiety. In a more preferred method, the clearing agent is a monoclonal antibody that is an anti-idiotypic to the monoclonal antibody of the conjugate used in the first step, as described in U.S. application Ser. No. 08/486,166. In another preferred embodiment, the clearing agent is substituted with multiple residues of carbohydrate, such as galactose, which allow the clearing agent to be cleared quickly from circulation by asialoglycoprotein receptors in the liver.

A physiological solution of the targeting species is advantageously metered into sterile vials, e.g., at a unit dosage of about 1.0–500 mg targeting species/vial, and the vials are either stoppered, sealed and stored at low temperature or lyophilized, stoppered, sealed and stored.

Variations and modifications of these formulations will be readily apparent to the ordinary skilled artisan, as a function of the individual needs of the mammal or treatment regiment, as well as of variations in the form in which radioisotopes may be provided or may become available.

Routes of administration include intravenous, intraarterial, intrapleural, intraperitoneal, intrathecal, subcutaneous or by perfusion.

Methods useful for internal detection or treatment of tumors or other lesions, such as cardiovascular lesions (clots, emboli, infarcts, etc.), infectious diseases, inflammatory diseases, and autoimmune diseases are disclosed in U.S. Pat. Nos. 4,782,840 4,932,412 and 5,716,595, the disclosures of which are incorporated herein by reference. The methods of the present invention can be used to enhance the methods disclosed in these references. The present invention also may be practiced in conjunction with intraoperative probes, endoscopic and laparoscopic uses, and in methods for imaging normal organs. The methods of the present invention can be used in other methods that will be apparent to those skilled in the art.

Examples of therapeutic agents include antibodies, antibody fragments, drugs, toxins, nucleases, hormones, immunomodulators, chelators, boron compounds, photoactive agents or dyes and radioinuclides.

In a further preferred embodiment, the cMORF is conjugated to a bifunctional chelator which in turn, is radiolabeled with an isotope. A chelator is radiolabeled first prior to conjugation (preconjugation labeling) to a protein, a polypeptide or an oligonucleotide which cannot withstand harsh conditions. Examples of chelators may include hydrazino nicotinamide (HYNIC), diethylenetriaminepentaacetic acid (DTPA), 1, 4, 7, 10-tetraaza-cyclododecane N, N', N", N'''-tetraacetic acid (DOTA), and mercaptoacetylglycylglycylglycine ($MAG_3$). A preferred bifunctional chelator used in the present invention is N-hydroxysuccinimidyl derivative of acetyl-S-protected mercaptoacetyltriglycine (NHS-$MAG_3$). NHS-$MAG_3$ is synthesized according to the method of Winnard, P. et al., *Nucl. Med. Biol.* 24:425–32 (1997). The conjugation of single-stranded morpholino oligomers with NHS-$MAG_3$ was accomplished as described in Mardirossian, G. et al., *J. Nucl. Med.* 38:907–13 (1997).

Radionuclides useful as therapeutic agents, which substantially decay by beta-particle emission include, include but are not limited to P-32, P-33, Sc-47, Fe-59, Cu-64, Cu-67, Se-75, As-77, Sr-89, Y-90, Mo-99, Rh-105, Pd-109, Ag-111, I-131, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213. Maximum decay energies of useful beta-particle-emitting nuclides are preferably 20–5,000 kcV, more preferably 100–4,000 kcV, and most preferably 500–2,500 keV.

Radionuclides useful as therapeutic agents, which substantially decay with Auger-emitting particles include, but are not limited to Co-58, Ga-67, Br-80m, Tc-99m, Rh-103m, Pt-109, In-111, Sb-119, I-125, Ho-161, Os-189m and Ir-192. Maximum decay energy of these radionuclides is preferably less than 1,000 keV, more preferably less than 100 keV, and most preferably less than 70 keV.

Radionuclides useful as therapeutic agents, which substantially decay with generation of alpha-particles include, but are not limited to Dy-152, At-211, Bi-212, Ra-223, Rn-219, Po-215, Bi-21 1, Ac-225, Fr-221, At-217, Bi-213 and Fm-255. Decay energies of useful alpha-particle-emitting radionuclides are preferably 2,000–9,000 keV, more preferably 3,000–8,000 keV, and most preferably 4,000–7,000 keV.

Metals useful, as complexes, as part of a photodynamic therapy procedure include, but are not limited to zinc, aluminum, gallium, lutetium and palladium.

Radionuclides useful in therapies based on neutron capture procedures include, but are not limited to B-10, Gd-157 and U-235.

Useful diagnostic agents include, but are not limited to radionuclides, dyes (such as with the biotin-streptavidin complex), contrast agents, fluorescent compounds or molecules and enhancing agents (e.g. paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radionuclides, enhancing agents for use in magnetic resonance imaging, and fluorescent compounds.

Radionuclides useful as diagnostic agents that are used in positron emission tomography include, but are not limited to F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124. Total decay energies of useful positron-emitting radionuclides are preferably less than 2,000 keV, more preferably under 1,000 keV, and most preferably less than 700 keV.

Metals useful in diagnostic agents utilizing magnetic resonance imaging techniques include, but are not limited to gadolinium, manganese, iron, chromium, copper, cobalt, nickel, dysprosium, rhenium, europium, terbium, holmium and neodymium.

Radionuclides useful as diagnostic agents utilizing gamma-ray detection include, but are not limited to Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20–2000 keV, more preferably 60–600 keV, and most preferably 100–300 keV.

The embodiments of the invention may be further illustrated through examples which show aspects of the invention in detail. These examples illustrate specific elements of the invention and are not to be construed as limiting the scope thereof.

EXAMPLES

Materials and Methods

The MORFs used in the present invention are obtained from Gene Tools, LLC. (Corvallis, Oreg.). They include a 15-mer (5' equivalent TGT-ACG-TCA-CAA-CTA-linker-amine (herein MORF15), and TAG-TTG-TGA-CGT-ACA-linker-amine (herein complementary MORF15 or cMORF15)), an 18-mer (5' equivalent CGG-TGT-ACG-TCA-CAA-CTA-linker-amine (herein MORF 18) and TAG-TTG-TGA-CGT-ACA-CCC-linker-amine (herein complementary MORF18 or cMORF18)), and a 25-mer (5' equivalent T-GGT-GGT-GGG-TGT-ACG-TCA-CAA-CTA-linker-amine (herein MORF25), and TAG-TTG -TGA-CGT-ACA-CCC-ACC-ACC-A-linker-amine (herein complementary MORF25 or cMORF25)). The linker used in the present invention is $H_2N-CH_2-CH(CH_2CH_2)_2N-COCH_2CH_2-CO-$. The molecular weights ranged from 5090 to 8568 Daltons. The cMORFs were occasionally purchased with a biotin group on the 3' end in place of the amine.

Streptavidin-coated magnetic beads (BioMag, Streptavidin Ultra-Load, Polysciences Inc Warrington, Pa.); 1-ethyl-3(3-dimethylaminopropyl)carbodiimide hydrochloride (EDC) (Pierce, Rockford, Ill.); the gel (Bio-Gel P-4 Gel, Medium) for separation (Bio-Rad Laboratories, Hercules, Calif.) and the Sephadex G100 resin (Pharmacia Biotech, Uppsala, Sweden) were purchased and used as received. All other chemicals were reagent grade and were used without purification. The $^{99m}$Tc-pertechnetate was eluted from a $^{99}$Mo-$^{99m}$Tc generator (Dupont, Billerica, Mass.).

The bifunctional chelator, N-hydroxysuccinimidyl derivative of acetyl-S-protected mercaptoacetyl-triglycine (NHS-MAG$_3$), was synthesized according to the method of Winnard, P. et al., Nucl. Med. Biol. 24:425–32 (1997). The structure was confirmed by elemental analysis, proton NMR, and mass spectroscopy. To 0.97 ml of a 0.225 M sodium hydroxide was added 50 mg of triglycine (264 μmol) and 10 μl of a freshly-prepared 50 mM disodium ethylenetriaminetetracetic acid (EDTA). This solution was passed through a 0.2 um filter to remove amine-containing particulates. A solution of 90 mg (390 μmol) of S-acetylthioglycolic acid N-hydrosuccinimide ester (SATA) in 340 μl of dimethyformamide (DMF; dried over molecular sieve) was prepared and was added dropwise to the stirred triglycine solution. After 15 min of stirring at room temperature, the non-aqueous solution was adjusted from an apparent pH of 8.9 to an apparent pH of approximately 2.7 (measured with a glass electrode-pH meter) by the addition of 37.6 μl of 6 M hydrochloric acid. An initial pH of about 8.9 was selected to deprotonate the amine on triglycine (pK 7.9; Fasman, G. D. [ed.] 1976, CRC Handbook of Biochemistry and Molecular Biology, Third Edition, Vol. I, p 321, CRC Press, Boca Raton, Fla.) but without reaching extreme basic pH values in which the acetyl group on SATA may hydrolyze. The pH was lowered as soon as possible to minimize hydrolysis of the acetyl group.

A solution of 60 mg (290 μmol) of dicyclohexylcarbodiimide (DCC) in 3.6 ml of dry DMF was added rapidly to the stirred triglycine/SATA solution (apparent pH of about 5.0). The solution became cloudy within 2 min. as dicyclohexylurea began to precipitate. The reaction was stirred at room temperature in the dark for 2–4 hrs and was then cooled to −20° C. for an additional hour to encourage complete precipitation. After centrifugation at 4° C., 2500 g for 15 min., the clear supernatant was removed.

Due to the presence of water in the DMF solution, the NHS-MAG$_3$ preparation in this form was always used within 24 hours of preparation. For long-term storage, the NHS-MAG$_3$ water/DMF solution was evaporated to near-dryness in 15–30 min. on a rotary flash evaporator (Rotavapur-R, Buchi, Switzerland) and was then lyophilized to dryness within 1 hr on a lyophilizer (Virtis, Gardenier, N.Y.). After drying in this fashion, the NHS-MAG$_3$ can be stored indefinitely at room temperatures in a dessicator. When using the dry, powdered NHS-MAG$_3$ for conjugation, an arbitrary value of 50% by weight was assumed for its purity.

Size exclusion (SE) HPLC analysis was performed on a Superose-12 column (HR10/30, Amersham Pharmacia Biotech) with 0.10 mol/L phosphate buffer pH 7.0 as eluant at a flow rate of 0.6 mL/min. In-line UV absorbance at 260 nm and radioactivity detectors were used to identify and quantitate peak fractions. Recovery of radioactivity was determined routinely.

Example 1

Coupling of MN-14 with MORF15 AND MORF18

A solution of murine anti-CEA IgG antibody MN-14 (IgG$_1$ subtype, MW 150-kDa) was prepared at a concentration of 1000 μg/83 μL in phosphate buffered saline (pH 7.0–7.2) and was conjugated with either MORF15 (500 μg/250 μL) or MORF18 (600 μg/250 μL) in 2-(N-morpholino)ethane sulfonic acid (MES), pH 5.0, in the presence of 1-ethyl-3(3-dimethylaminopropyl)carbodiimide (EDC) in water (1000 μg/50 μL). The above mixture was incubated at room temperature for at least 1 hour.

Purification was achieved on a 0.7×20 cm Sephadex G-100 column with 0.05 mol/L, pH 7.0 phosphate buffer as eluant. The concentration of the recovered fraction(s) was estimated with respect to MN14 by UV absorbance at 280 nm using the absorbance coefficient of 1.40 μL/μg.

The antibody-MORF conjugates were characterized in terms of antibody concentration and MORF group per molecule. Previously, groups per molecule were estimated by adding increasing amounts of radiolabeled-cMORF to the conjugated antibody followed by size exclusion HPLC analysis to establish the saturation point by a shift in the radioactivity profile to that of free cMORF. Liu, G. et al., J. Nucl. Med. 43:384–391 (2002). In this present investigation, an alternative and more accurate method using UV absorbance was employed. The separate absorbance profiles of native MN14, free MORF15 and free MORF18 were first measured in the range of 200 to 300 nm using a scanning UV spectrophotometer (U-2000, Hitachi Instruments, Inc, Danbury, Conn.). It was therefore determined that the maximum absorbance of MN14 is at 280 nm while that of both MORFs is at 265 nm. Because the MORF-conjugated MN14 contained traces of free MORF even after purification, the measurement was performed during HPLC separation. Thus standard curves were constructed by HPLC-dual UV analysis in which the absorbance of native MN14 and native MORF15 at both 280 nm and 265 nm were measured. Under the assumption that the absorbance coefficients of MN14 and MORF does not change after conjugation, the concentration of MN14 and the MORF groups per molecule was calculated by measuring the absorbance at both wave lengths during HPLC analysis of the conjugated antibody. The concentration of MN14 and the MORF groups per MN14 in each MN14-MORF sample was calculated according to the following equations:

$$H^{280} = H^{280}{}_{MN14} + H^{280}{}_{MORF}$$

$$H^{265} = H^{265}{}_{MN14} + H^{265}{}_{MORF}$$

$$H^{280}{}_{MN14} = k^{280}{}_{MN14} W_{MN14}$$

$$H^{280}{}_{MORF} = k^{280}{}_{MORF} W_{MORF}$$

$$H^{265}{}_{MN14} = k^{265}{}_{MN14} W_{MN14}$$

$$W_{MORF} = \left(\frac{H^{265}}{k^{265}_{MN14}} - \frac{H^{280}}{k^{280}_{MN14}}\right) \Big/ \left(\frac{k^{265}_{MORF}}{k^{265}_{MN14}} - \frac{k^{280}_{MORF}}{k^{280}_{MN14}}\right) \quad \text{Equation 1}$$

$$W_{MN14} = \left(\frac{H^{265}}{k^{265}_{MORF}} - \frac{H^{280}}{k^{280}_{MORF}}\right) \Big/ \left(\frac{k^{265}_{MN14}}{k^{265}_{MORF}} - \frac{k^{280}_{MN14}}{k^{280}_{MORF}}\right) \quad \text{Equation 2}$$

Concentration of $MN14 = W_{MN14}$/volume applied    Equation 3

MORF number per $MN14 = (W_{MORF}/M_{MORF})/(W_{MN14}/M_{MN14})$    Equation 4 where H represents peak height in absorbance units (AU), W is weight ($\mu$g), M is molecular weight (Da), and k is the slope of standard curve (AU/$\mu$g).

FIG. 1A presents profiles at 280 nm obtained by HPLC analysis of the conjugated and purified MN14-MORF15 (left panel) and MN14-MORF18 (right panel) used in this investigation. The chromatograms at 265 nm are basically the same except for minor differences in peak heights (data not shown). In both panels, several small peaks are present. Those to the left of the main peak are higher molecular weight impurities possibly due to cross linking while that to the right is due to free MORF.

Figure 1B:
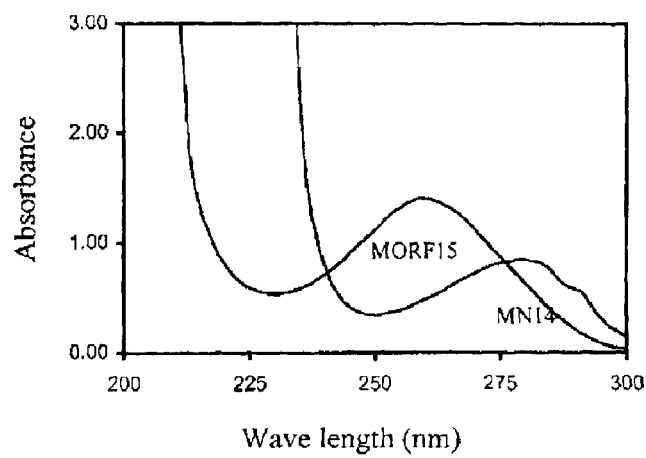
Figures 1C, 1D:
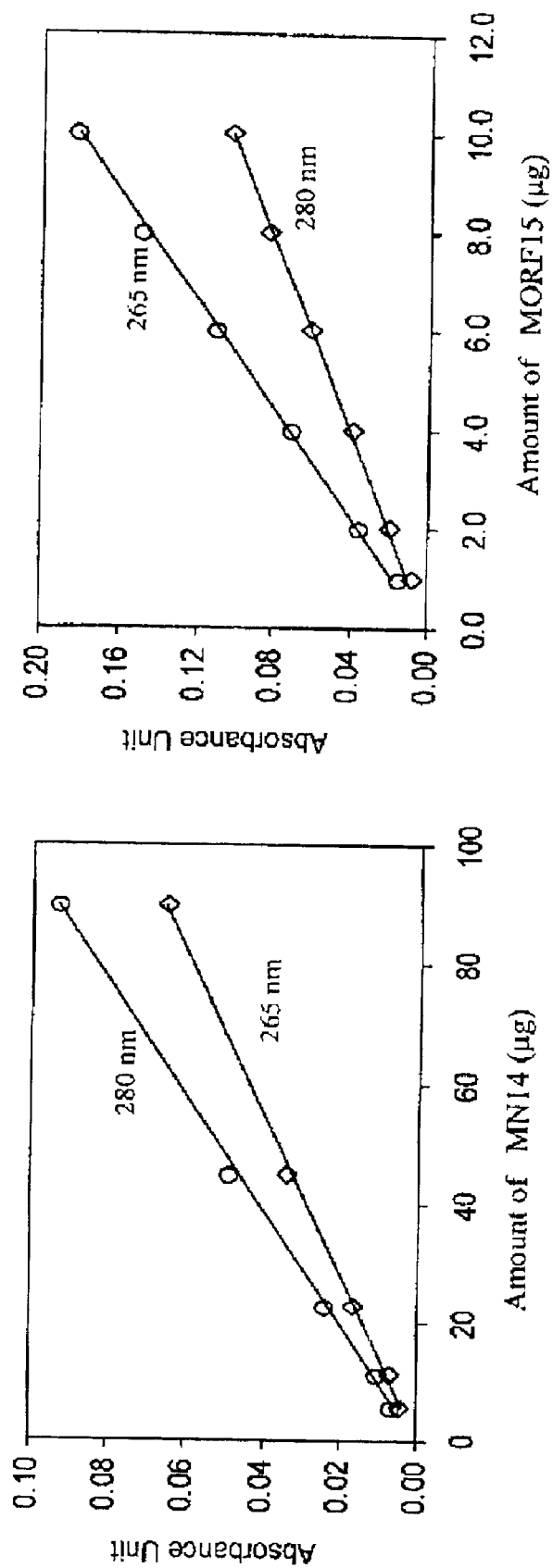

The UV spectra of both MN14 and MORF15 are shown in FIG. 1B. Overlap of the 265 nm peak of MORF 15 and the 280 nm peak of MN14 is clearly demonstrated. Nevertheless, it is possible to determine accurately the weight of MORF and the weight of MN14 in a sample of MORF-conjugated MN14 by measuring absorption at both wave lengths and by calculating the weights of both MORF and MN14 in the protein peak using Equations 1 and 2. FIGS. 1C and 1D present standard absorption curves for native MN14 and native cMORF15. Both curves are linear at least within the range studied (i.e. 0–100 $\mu$g for MN14 and 0–10 $\mu$g for MORF) with slopes of 0.00104 AU/$\mu$g and 0.00073 AU/$\mu$g for MN14 and 0.01022 AU/$\mu$g and 0.01816 AU/$\mu$g for MORF15 at 280 nm and 265 nm, respectively. The standard curves of MORF18 and MORF25 (not shown) are quite similar with slopes of 0.00738 and 0.00749 AU/$\mu$g and 0.01287 and 0.01314 AU/$\mu$g for MN14 and MORF15 at 280 nm and 265 nm, respectively. From Equations 1, 2, and 4, the MORF groups per MN14 for the MN14-MORF15 and MN14-MORF18 conjugates used in the present invention were calculated to be identical at 0.28±0.1 and 0.27±0.1 groups per molecule, respectively. The concentrations of conjugated antibody was also calculated using Equations 1, 2 and 3.

Example 2

Coupling of cMORF15 and cMORF18 to NHS-MAG$_3$

The conjugation of cMORF15 and cMORF18 with NHS-MAG$_3$ was accomplished as described in Mardirossian, G. et al., *J. Nucl. Med.* 38:907–13 (1997) and Wang, Y. et al. *Bioconj. Chem.* 12:807–816 (2001). NHS-MAG$_3$ powder (410 $\mu$g) was conjugated to both cMORF15 and cMORF18 (880 $\mu$g/200 $\mu$L) in 0.2M HEPES, pH 8. Fifty microliters of HEPES was added to the resulting mixture and incubated for 4 hours. CMORFs (880 $\mu$g) were dissolved in 250 $\mu$l of 0.2 M HEPES buffer (pH 8.0) and were added to a vial containing 1150 $\mu$g of solid NHS-MAG$_3$. After vortexing, the mixture was incubated at room temperature for at least 1 hr. The molar ratio of MORF18 to NHS-MAG$_3$ was about 1:20. The incubated solution was separated on a 0.7×20 cm column of P4 with an eluant of 0.25 M ammonium acetate buffer, pH 5.2. The concentration with respect to cMORF of the recovered fractions were estimated by UV absorbance at 265 nm using an absorbance coefficient of 31 $\mu$L/$\mu$g. The peak fractions were identified by Uv spectrophotometry at 265 nm and were stored in a freezer at −20° C.

The coupling mixture was purified on a P4 column (0.7×20 cm; BioRad, Melville, N.Y.) using ammonium acetate (0.25 M, pH 5.2) as the eluent. The cMORF15-MAG$_3$ and cMORF18-MAG$_3$ peaks were determined by UV absorption at 260 nm using an extinction coefficient of 31.1 $\mu$L/$\mu$g.

Example 3

Radiolabeling of cMORF15-MAG$_3$ and cMORF18-MAG$_3$

Twenty-five microliters of cMORF15-MAG$_3$ and cMORF18-MAG$_3$ (0.25 M ammonium acetate, pH 5.2) was mixed with 6 $\mu$L sodium tartrate solution (50 mg/ml of fresh sodium tartrate in 0.5 M sodium bicarbonate, 0.25M ammonium acetate, 0.18 ammonium hydroxide, pH 9.2). This was followed by adding 20 $\mu$L of about 5 mCi of $^{99m}$Tc-pertechnetate generator eluant. Finally, 2 $\mu$L tin(II) chloride (1 $\mu$g /$\mu$L in 10 mM HCl; Sigma) was quickly added by agitation. The conjugates were capped and placed in a boiling water bath for 20–30 min.

After 5–15 minutes at room temperature, the labeled-cMORFs-MAG$_3$ was purified on a P4 column (0.7×20 cm) with 0.05 M phosphate buffer, pH 7 as the eluant. The peak was identified by counting fractions in a dose calibrator. The purified product was analyzed by size-exclusion HPLC using a Superose-12 (Pharmacia, Piscataway, N.J.). FIG. 1 represents a size exclusion HPLC radiochromatogram showing that the peak-times for both cMORF18-MAG$_3$-$^{99m}$Tc and cMORF15-MAG$_3$-$^{99m}$Tc were 30.8 min and 31.2 min, respectively.

Quality Assurance of Labeled-cMORF18

Figure 2:
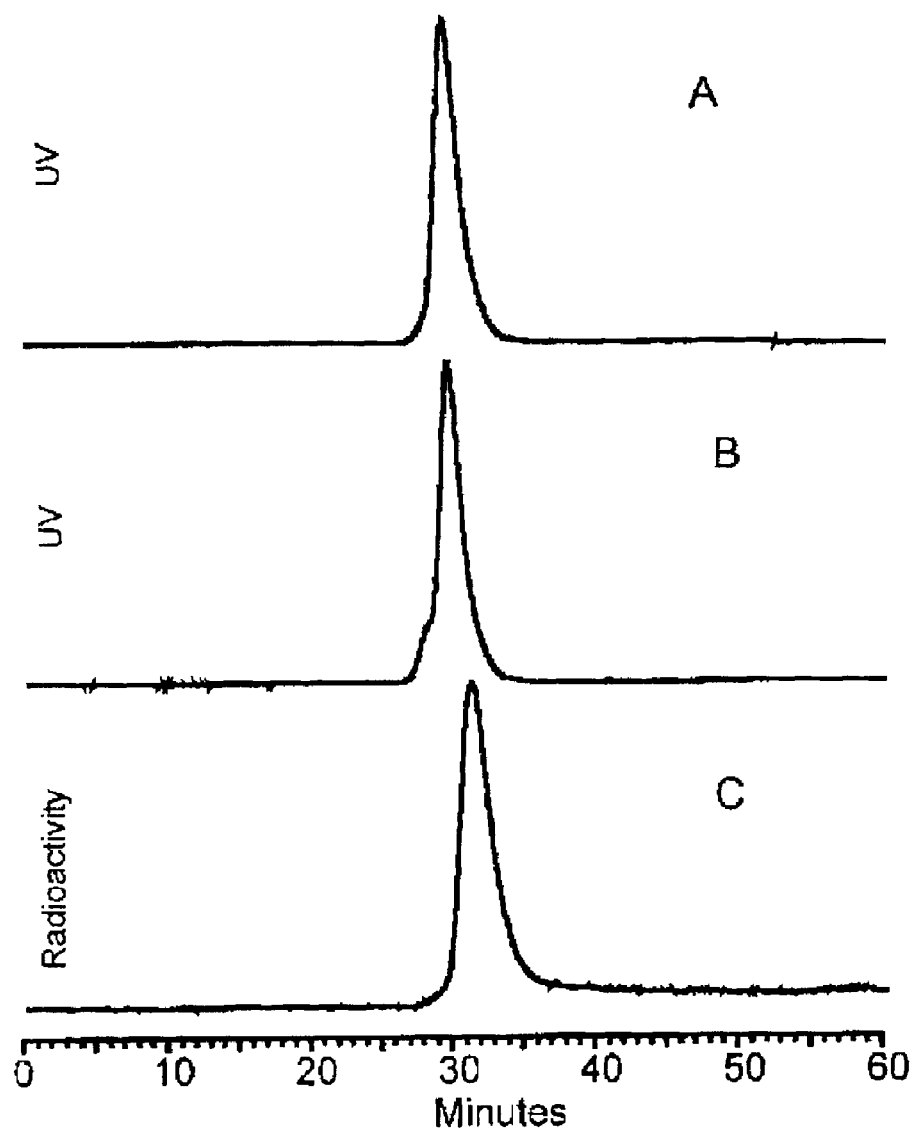
FIG. 2. UV (260 nm) size exclusion HPLC profiles of uncoupled, native cMORF18 (A), MAG$_3$-coupled cMORF18 (B), and radioactivity profile of $^{99m}$Tc-labeled MAG$_3$-cMORF18 (C).

FIG. 2 presents UV chromatograms of native cMORF18 (FIG. 2A), MAG$_3$-coupled cMORF18 (FIG. 1B), and radiochromatogram of $^{99m}$Tc-MAG$_3$-cMORF18 (FIG. 2C). The labeling efficiency of labeled-cMORF18 was between 40%-60%. The radioactivity recovery of labeled-cMORF18 off the HPLC was always over 90%. The retention time of both native and coupled-cMORF18 is 29.5 min, however the latter shows a small shoulder with a retention time at about 28 min (possibly a result of MAG$_3$-cMORF18 dimer formation through disulfide bonds). The radiolabeled-cMORF18 shows a slightly longer retention time of 31.1 min.

Hybridization Ability of $^{99m}$Tc-Labeled-cMORF18

Binding to beads is a convenient method to evaluate hybridization between an oligomer and its complement. Mardirossian, G. et al., *J. Nucl. Med.* 38:907–13 (1997) and Wang, Y. et al. *Bioconj. Chem.* 12:807–816 (2001). After optimization of hybridization conditions, the hybridization ability of radiolabeled-cMORF18 was evaluated on streptavidin-coated magnetic beads.

Beads (300 μL) were washed three times with 200 μL of washing buffer (20 mmol/L Tris buffer-0.5 mol/L sodium chloride, pH 8.2). The beads were retained in the tube during washing by using a magnetic separator (MPC, Dynal, A. S., Lake Success, N.Y.). After the last wash, the beads were suspended in 200 μL of the washing buffer, 1.0 μg biotin-MORF18 was added and, 15 min later, the beads were washed three times again each with 200 μL of the washing buffer. After resuspension in 200 μL washing buffer, 2 μL radiolabeled-ORF18 (0.02 μg cMORF18) was added. After 1 h of incubation with constant agitation, the beads were separated, washed three times and counted in a NaI(T1) well counter. The supernatant and washing solutions were combined and counted. Two control groups, one without biotin-MORF18 and one in which biotin-cMORF18 substituted for biotin-MORF18, were simultaneously carried through the identical procedure.

Under the conditions of the bead study, 90.2±0.9% (n=3) of the labeled-cMORF18 bound to MORF18 beads compared to only 0.4±0.1% and 0.3±0.1% (n=3) of the labeled-cMORF18 in the case of the blank control and the biotin-cMORF18 control, respectively. The radioactivity on beads in the study group therefore is due to hybridization of labeled-cMORF18 to MORF18 on the beads. These hybridization results of $^{99m}$Tc-MAG$_3$-cMORF (18 mer) to MORF (18 mer) on beads agree with earlier findings on hybridization on beads of a $^{99m}$Tc-MAG$_3$-MORF(15 mer) to cMORF (15 mer) (Mang'era, K. O. et al. *Eur. J Nucl. Med.* 28:1682–1689 (2001).

The single peak observed for labeled-cMORF18 by HPLC (FIG. 2C) and the fact that at least 90% of the radioactivity hybridized to its complement in the bead study indicate that coupling with NHS-MAG$_3$, purification on the P4 column, labeling with $^{99m}$Tc, and purification again on the P4 column provided a satisfactory radiolabeled-cMORF18.

Estimation of MORF18 Groups Per Molecule on Coupled-MN14

After coupling, the MORF18 on MN14 could not be detected by its UV absorbance. To estimate the number of MORF18 groups on MN14, a series of aliquots of purified radiolabeled-cMORF18 (4, 25, 50, 150 μL at 0.01 μg/μL) were added to 50 μL of MN14-MORF18 (0.5 μg/μL), incubated at room temperature for 1 h and analyzed by SE HPLC. A control study was performed identically with 4 μL (0.01μg/μL) of radiolabeled-cMORF18 but added to native MN14. Using SE HPLC, radioactivity bound to MN14 is detected readily by the shift in radioactivity profile to higher molecular weight (earlier retention times) from labeled-cMORF to labeled-cMORF18-MN14-MORF 18.

Figure 3:
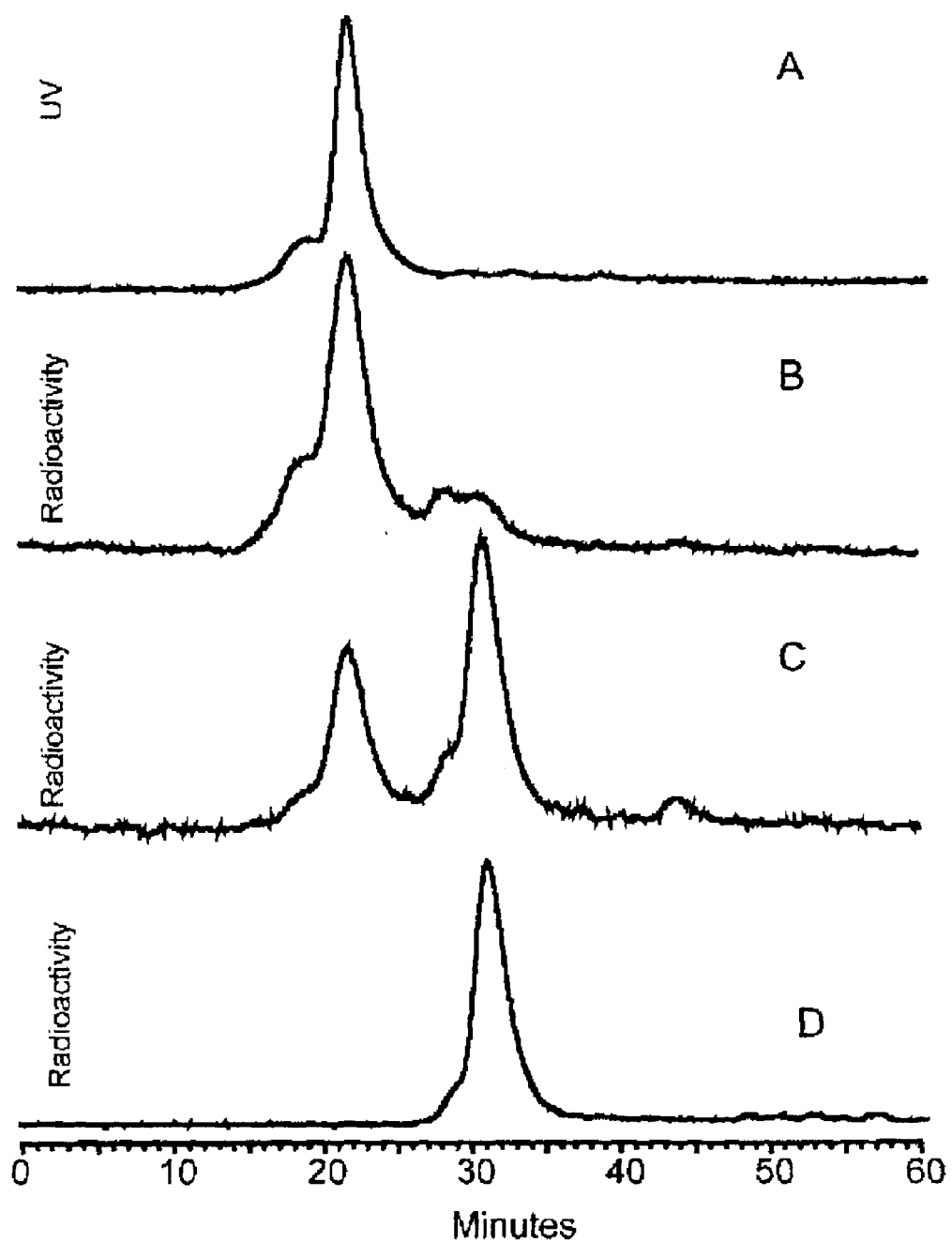
FIG. 3. UV (260 nm) size exclusion HPLC profiles of MN14-MORF18 (A) and radioactivity profiles of labeled-cMORF18 added to MN14-MORF18 at weight ratios of 0.04 µg/25 µg (B) and 0.25 µg /25 µg (C), respectively. Also shown is the radioactivity profile of labeled-cMORF18 added to native MN14 as control. (D). The extent of MN14 binding decreases as the weight of labeled-cMORF 18 increases.

FIG. 3 presents HPLC profiles obtained by the hybridization of MN14-conjugated MORF18 with labeled-cMORF18. Recovery of radioactivity was over 90%. The Uv chromatogram of MN14-MORF18 is presented for reference (FIG. 3A) along with the radioactivity profile of a mixture of 50 μL (25 μg) of native MN14 and 4 μL (0.04 μg) of labeled-cMORF18 (FIG. 3D). When the same weight of labeled-cMORF18 is now added to the same weight of MN14-MORF18 instead of native MN14, a shift of at least 80% to higher molecular weight is evident (FIG. 3B). The 20% remaining is composed of two peaks, one with a retention time that corresponds to labeled-cMORF18 and another with the same retention time as a hybridized duplex of MORF18 and labeled-cMORF18 (data not presented). Thus, the two peaks are probably due respectively to traces of free labeled-cMORF18 and labeled-cMORF18 hybridized to free MORF18 not removed during the purification of the MN14 preparation. That 80% of labeled-cMORF18 binds to MN14 demonstrates that MORF18 has been coupled successfully to the antibody and is still capable of hybridizing. Native MN14 does not bind $^{99m}$Tc-MAG$_3$-cMORF18 (FIG. 3D).

FIG. 3 also presents radiochromatograms of a mixture of 25 μL (0.25 μg) labeled-cMORF18 and 50 μL (25 μg) MN14-MORF18 (FIG. 3C). More than half of the radioactivity is not hybridized under these conditions. Increasing the dosage of labeled-cMORF18 to 50 μL or 150 μL increases the relative size of the peak of free $^{99m}$Tc-MAG$_3$-cMORF18 as the MORF18 molecules on MN14 become saturated.

Example 4

Biodistribution of Labeled-cMORF in Normal CD-1 Mice

Twelve normal CD-1 mice (30–35 g) each received 1.5 μg (3.7 MBq) of labeled-cMORF18 by tail vein injection. Four mice were sacrificed at each of 0.5, 1.0, and 3.0 h. The mice were dissected, urine was carefully drawn and organs were removed and weighed. The radioactivity in each organ was counted in the NaI(T1) well counter along with blood samples of known volume and an aliquot of the injectate. The radioactivity remaining in the carcass was measured in a dose calibrator.

Table 1 lists the biodistribution results of $^{99m}$Tc in normal CD-1 mice at three time-points 0.5, 1.0, and 3.0 h after injection of $^{99m}$Tc-cMORF18. The whole body radioactivity remaining (not including urine) was 23%, 12% and 7% ID respectively at these points. There was no significant uptake in liver, small intestines, and large intestines, indicating that the labeled-cMORF18 is almost solely excreted through the kidneys. Highest radioactivity levels were in kidneys at 6–7% ID/g throughout. At 0.5 h, the blood level (0.7% ID/g) was relatively high, but at 1 h, blood and all other organs except kidneys were <0.2% ID/g.

TABLE 1

Biodistribution of $^{99m}$Tc-cMORF18 in normal mice (% ID/g) (n = 4)

| Organ | 0.5 h | | 1.0 h | | 3.0 h | |
|---|---|---|---|---|---|---|
| | Mean | SD | Mean | SD | Mean | SD |
| Liver | 0.23 | 0.06 | 0.15 | 0.02 | 0.15 | 0.04 |
| Heart | 0.22 | 0.07 | 0.07 | 0.01 | 0.04 | 0.01 |
| Kidneys | 6.1 | 0.75 | 7.1 | 0.57 | 6.4 | 1.02 |
| Lungs | 0.42 | 0.09 | 0.15 | 0.02 | 0.07 | 0.01 |
| Spleen | 0.16 | 0.02 | 0.10 | 0.02 | 0.09 | 0.02 |
| Muscle | 0.17 | 0.04 | 0.09 | 0.07 | 0.02 | 0.01 |
| Blood | 0.74 | 0.18 | 0.18 | 0.05 | 0.04 | 0.01 |
| Whole body in ID % | 22.5 | 4.4 | 11.7 | 2.3 | 7.0 | 1.0 |

Example 4

Biodistribution of Labeled-cMORF18 in Tumored Nude Mice

Biodistribution data in Table 2 show that, with the exception of kidneys, radioactivity accumulated primarily in tumor with values of 1.7–1.8% ID/g and that the radiolabel was retained in tumor over this period. Whole body radioactivity levels for the study animals were 14% and 11% ID at 3 h and 24 h while these values for the control animals were 7% and 5% ID (in all cases with radioactive urine removed).

TABLE 2

Biodistribution of $^{99m}$Tc-cMORF18 in LS174T Tumor Bearing Nude Mice (% ID/g) (n = 4)

| Organ | 3 h | | | | 24 h | | | |
|---|---|---|---|---|---|---|---|---|
| | Control | | Study | | Control | | Study | |
| | Mean | SD | Mean | SD | Mean | SD | Mean | SD |
| Liver | 0.23 | 0.01 | 0.41 | 0.05 | 0.10 | 0.01 | 0.60 | 0.05 |
| Heart | 0.04 | 0.01 | 0.18 | 0.01 | 0.02 | 0.00 | 0.13 | 0.02 |
| Kidneys | 6.4 | 1.95 | 6.9 | 1.96 | 3.2 | 0.68 | 4.0 | 1.00 |
| Lungs | 0.07 | 0.01 | 0.34 | 0.06 | 0.04 | 0.01 | 0.24 | 0.04 |
| Spleen | 0.11 | 0.01 | 0.29 | 0.08 | 0.07 | 0.01 | 0.31 | 0.04 |
| Muscle | 0.03 | 0.03 | 0.09 | 0.01 | 0.02 | 0.00 | 0.07 | 0.01 |
| Tumor | 0.09 | 0.01 | 1.8 | 0.24 | 0.05 | 0.00 | 1.7 | 0.14 |
| Blood | 0.04 | 0.01 | 1.02 | 0.13 | 0.00 | 0.01 | 0.50 | 0.12 |
| Whole body in ID % | 6.9 | 3.3 | 14.4 | 0.9 | 5.0 | 2.0 | 11.4 | 0.7 |

Figure 4:
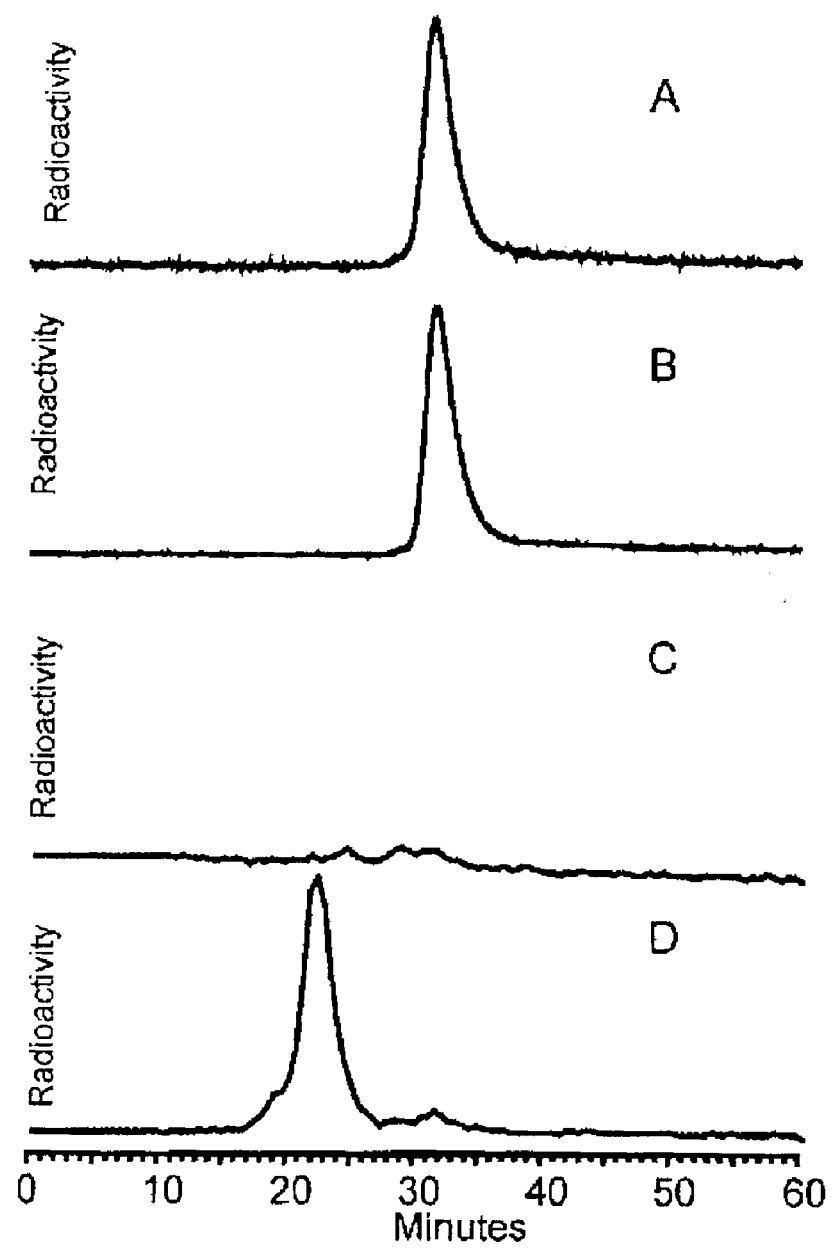
FIG. 4. Size exclusion radioactivity HPLC profiles of urine obtained at 3 h from a control mouse receiving only labeled-cMORF18 (A) and a study mouse receiving both MN14-MORF18 and labeled-cMORF18 (B). Also presented are radiochromatograms on the same axes of plasma obtained at 3 h from a control mouse (C) and from a study mouse (D). The results show that radioactivity in urine is present primarily as labeled-cMORF18, while in plasma, significant levels of radioactivity are present only in study mice and then only as the labeled-cMORF18-MN14-MORF18 complex.

FIG. 4 presents HPLC radiochromatograms of urine at 3 h obtained from a control animal (FIG. 4A) and from a study animal (FIG. 4B). These results suggest that radioactivity in urine was present as intact labeled-cMORF18 (FIG. 2C) and, therefore, that labeled-cMORF is stable in vivo.

FIG. 4 also presents radiochromatograms of plasma from a control animal (FIG. 4C) and a study animal (FIG. 4D) at 3 h. Because radioactivity levels were too low for measurement by the in-line radioactivity detector, fractions off the HPLC were collected for counting in a well NaI(T1) detector. In the figure, the axes have been adjusted so that retention times for all panels may be compared. There is no radioactive peak in plasma from the control animal (in FIG. 4C) whereas the radiochromatogram of plasma on the same scale from the study animal (FIG. 4D) shows only one radioactive peak corresponding in retention time to labeled-cMORF18 hybridized to MN14-MORF18 (FIG. 3B). The higher blood radioactivity in the study animals compared to the control (Table 2) indicates that a considerable amount of the radiolabeled antibody was still in circulation in the study animals after 48 h at the time when the labeled-cMORF18 was injected (as expected for an IgG antibody). In the absence of the antibody, the labeled-cMORF18 cleared rapidly as shown in the control animals.

Example 5

Pretargeting of Labeled-cMORF18 in LS174T Tumored Nude Mice

The LS174T tumor was obtained from the American Type Culture Collection and was grown in minimal essential medium (Gibco, Grand Island, N.Y.). The cells were removed from the culture flask by trypsinization and then washed in the culture media. Nude mice bearing LS174T tumor were prepared according to the protocol as disclosed by Rusckowski et al., Cancer 80:2699–705 (1997).

Eight nude mice (25–30 g) were each injected with $10^6$ LS174T colon tumor cells into one thigh. After 14 days when the tumors were no more than 1 cm in any dimension, half the animals each received 50 μg of MN14-MORF18. After 48 h, the mice in both groups received 1.0 μg of labeled-cMORF18 (7.4–8.9 MBq) via a tail vein. At 3 and 24 h post injection of labeled-cMORF18, animals were anesthetized with ketamine plus xylazine and imaged anteriorly with a large field of view scintillation camera (Elscint, Hackensack, N.J.). Immediately after imaging at 24 h, the mice were sacrificed and the biodistribution of the radiolabel was determined as described.

In an identical repeat study, the imaging was performed after sacrifice at 3 h and after carefully removing most of the urine with a syringe. Urine and plasma samples from mice sacrificed at 3 h were analyzed by SE HPLC, in the former case using in-line radioactivity detection and in the latter case by collecting fractions for counting in a NaI(T1) well counter.

Figure 5:
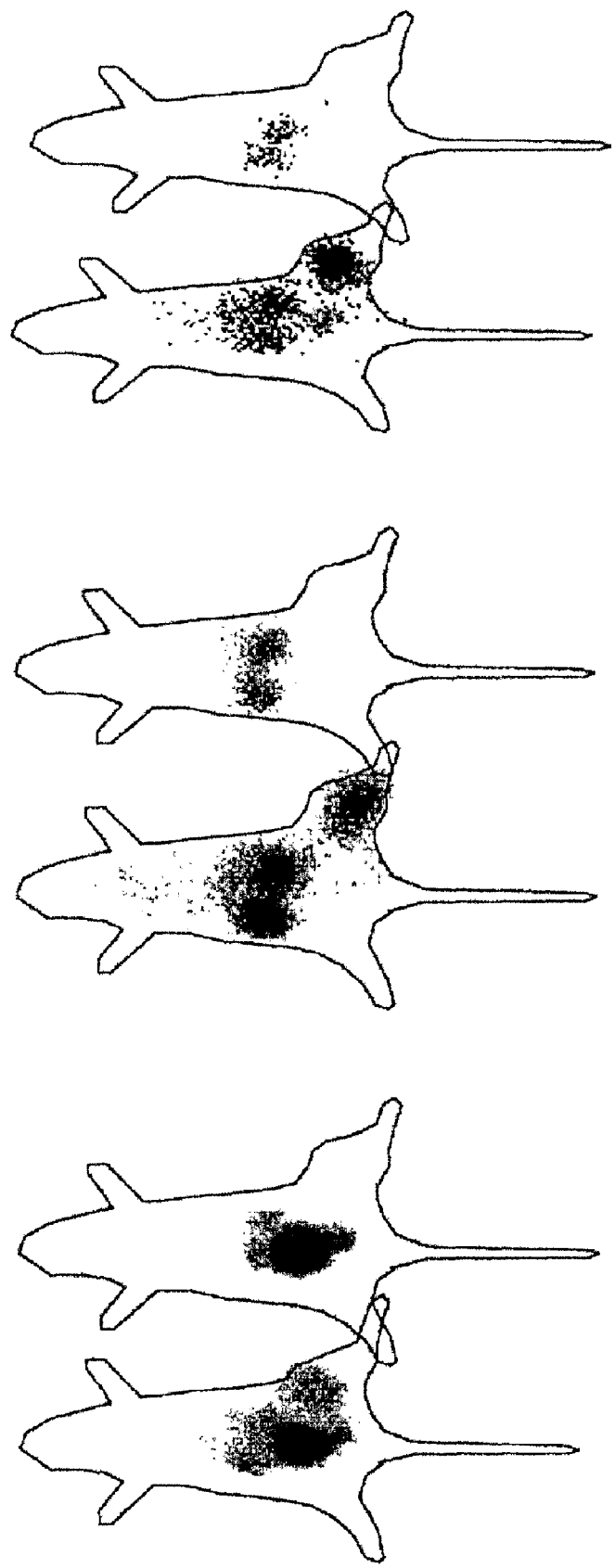
FIG. 5. Whole body anterior gamma camera images of LS174T tumor bearing nude mice obtained at 3 h (A) and 24 h (C) and the image obtained in a repeat study at 3 h (B) with prior removal of urine. In each image, the study animal is on the left and the control animal is on the right.

FIG. 5 presents whole body images at 3 h (FIG. 5A) and 24 h (FIG. 5C) after injection of labeled-cMORF18 to the tumored mice previously injected with MN14-MORF18 48 h earlier. The tumor in the study animal (left in each panel) is clearly seen in contrast to the control animal not receiving the MN14-MORF18 (right in each panel). In the early images (FIG. 5A), radioactivity in bladder is pronounced and at interfering levels. At 24 h however (FIG. 5C), urine activity has diminished so that the image now clearly shows only the tumor along with kidneys. A repeat study at 3 h (FIG. 5B) with imaging was performed with removal of the urine. Only the kidneys and tumor are prominent at this time. In all three images, tumor is not visible in the control animals.

Example 6

The Influence of Chain Length and Base Sequence on the Pharmacokinetic Behavior of $^{99m}$Tc-Morpholinos in Mice Pharmacokinetics of Labeled-cMORF15, cMORF18, cMORF25 and MORF15, MORF18, MORF25

Twelve normal CD-1 mice weighing 30–40 g (Charles River, Wilmington, Mass.) each received 0.3 μg (50–70 μCi) of the labeled-cMORF by tail vein injection. Four mice were sacrificed at each of 0.5, 1, and 3 hrs. The radioactivity in each organ and blood was counted in a NaI(T1) well counter along with an aliquot of the injectate. The radioactivity remaining in the carcass was measured in a dose calibrator.

Figure 6:
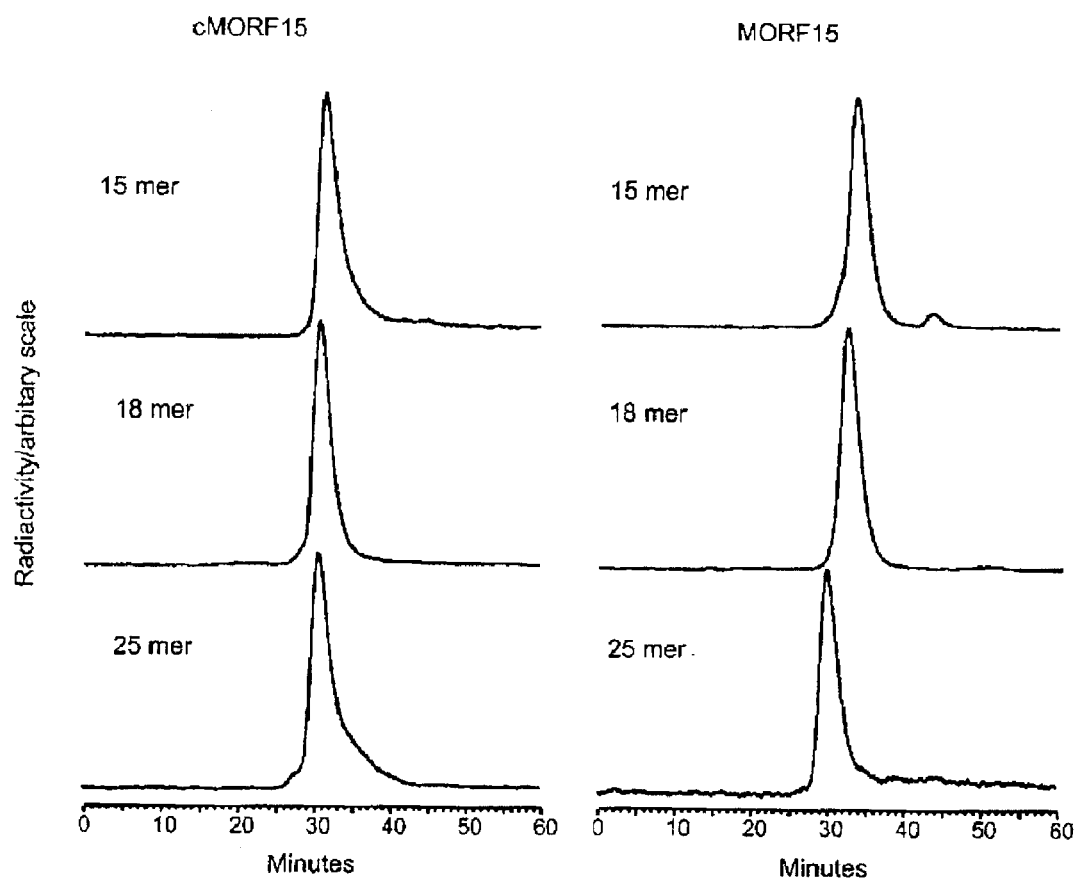
FIG. 6. Size exclusion HPLC radiochromatograms of $^{99m}$Tc-labeled-cMORF15, cMORF18, and cMORF25 and MORF15, MORF18, and MORF25.

Quality assurance of all the six labeled cMORFs was achieved by HPLC and by using beads. FIG. 6 present HPLC radiochromatograms of all six labeled MORFs and cMORFs showing in each case a single peak and with a relative retention time reflecting the slight differences in molecular weight (33.5, 32.3, and 29.9 min for MORF25, MORF18, and MORF15, respectively, and 31.3, 31.0, and 30.5 min for cMORF25, cMORF18, and cMORF15, respectively). Recovery in each case was greater than 90%. The hybridization of each $^{99m}$Tc labeled (c)MORF to its biotinylated complement immobilized on streptavidin beads was in all cases essentially quantitative (data not presented).

Figure 7:
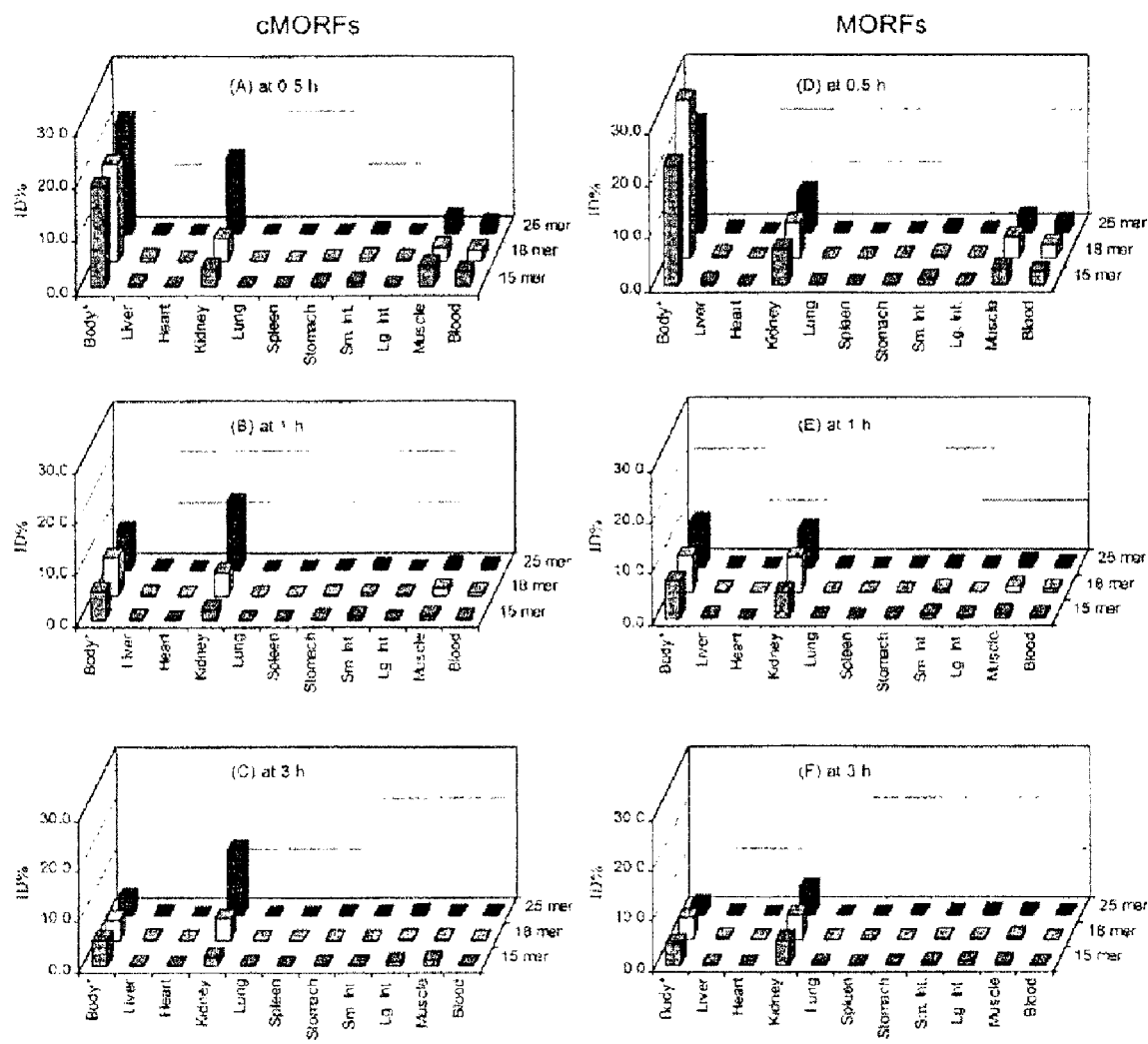
FIG. 7. Biodistribution of $^{99m}$Tc-labeled-cMORF15, cMORF18, and cMORF25 and MORF15, MORF18 and MORF25 at 0.5, 1, and 3 hrs. *Body=whole body radioactivity minus urine and kidney.

Tables 4 and 5 present the biodistributions in ID %/gm of $^{99m}$Tc at 0.5, 1.0 and 3.0 hrs post administration of labeled-cMORFs and MORFs to normal mice. FIG. 7 presents in histographic form the same biodistribution results but in ID % per organ. For all six cMORFs at 0.5 hrs, the radiolabel is still present in circulation as indicated by the relatively-high values in blood and muscle. Rapid clearance from circulation is also indicated in all cases by the decrease in these radioactivity levels at 1 hr. From 1 hr on, the only organs with high radioactivity levels are the kidneys, for all six cMORFs. Interestingly, the influence of chain length is pronounced only in the case of cMORF where kidney levels increase dramatically with increasing length at all times. For example, at 3 hrs, kidney values increase from 1.7 to 13.5 ID % for cMORF15 to cMORF25 respectively but remain fairly constant at 4.5 and 5.6 ID % for MORF15 to MORF25. In the case of cMORF25, kidney levels account for more than 80% of the whole body radioactivity at this time. The presence of high levels of radioactivity only in kidneys is in agreement with earlier studies of $^{99m}$Tc-labeled MORFs that showed rapid and almost exclusive clearance through the kidneys. Mang'era, K., et al., *Eur. J. Nucl. Med.* 28:1682–1689 (2001) and Liu G. et al., *J. Nucl. Med.* 43:384–391 (2002).

Pretargeting Using MN14-MORF15 and Labeled-cMORF15

The biodistributions in ID % per organ and target to non-target ratios at 3 hrs post administration of radiolabeled-cMORF15 or cMORF18 to tumored animals receiving MN14-MORF15 or MN14-MORF18 respectively 48 hrs earlier are presented in Table 6. Also presented are the results of administering radiolabeled-cMORF15 to control animals not having received the antibody. These data show the superiority of cMORF15-$^{99m}$Tc pretargeting over cMORF18-$^{99m}$Tc pretargeting. At 3 hrs, the biodistribution of cMORF15-$^{99m}$Tc in tumored nude mice by pretargeting (Table 6) is almost the same as that in normal CD-1 mice (Table 4) in that there is little uptake in all other organs except kidneys and intestines. There is also no large difference in radioactivity between 15 mer pretargeting and 18 mer pretargeting in all organs other than kidneys. Kidney radioactivity uptake of MN14-MORF18/cMORF18-$^{99m}$Tc pretargeting is almost twice that of MN14-MORF15/cMORF15-$^{99m}$Tc pretargeting. Because the tumor uptake is also higher for the 15 mer pretargeting, the tumor/normal tissue ratios are improved in all cases for 15 mer pretargeting. Slight differences in the MORF groups per antibody (0.28 vs. 0.27) and dosage administered (14 μg vs. 13 μg)

TABLE 4

Biodistribution of $^{99m}$Tc-cMORFs in normal mice (ID %/g, n = 4)

| | cMORF15-$^{99m}$Tc | | | cMORF18-$^{99m}$Tc* | | | cMORF25-$^{99m}$Tc | | |
|---|---|---|---|---|---|---|---|---|---|
| Organ | 0.5 h | 1 h | 3 h | 0.5 h | 1 h | 3 h | 0.5 h | 1 h | 3 h |
| Liver | 0.43 | 0.23 | 0.15 | 0.23 | 0.15 | 0.15 | 0.23 | 0.14 | 0.10 |
| | (0.17) | (0.07) | (0.02) | (0.06) | (0.02) | (0.04) | (0.03) | (0.02) | (0.02) |
| Heart | 0.60 | 0.10 | 0.04 | 0.22 | 0.07 | 0.04 | 0.25 | 0.10 | 0.05 |
| | (0.43) | (0.04) | (0.01) | (0.07) | (0.01) | (0.01) | (0.05) | (0.01) | (0.01) |
| Kidney | 7.76 | 4.90 | 4.13 | 6.10 | 7.10 | 6.40 | 23.84 | 21.86 | 20.94 |
| | (2.15) | (1.83) | (0.29) | (0.75) | (0.57) | (1.02) | (9.53) | (4.04) | (4.38) |
| Lung | 0.60 | 0.17 | 0.09 | 0.42 | 0.15 | 0.07 | 0.54 | 0.2 | 0.10 |
| | (0.21) | (0.05) | (0.01) | (0.09) | (0.02) | (0.01) | (0.03) | (0.02) | (0.00) |
| Spleen | 0.29 | 0.11 | 0.08 | 0.16 | 0.10 | 0.09 | 0.17 | 0.10 | 0.06 |
| | (0.11) | (0.03) | (0.03) | (0.02) | (0.02) | (0.02) | (0.02) | (0.01) | (0.01) |
| Muscle | 0.40 | 0.08 | 0.09 | 0.17 | 0.09 | 0.02 | 0.22 | 0.06 | 0.02 |
| | (0.17) | (0.02) | (0.07) | (0.04) | (0.07) | (0.01) | (0.02) | (0.01) | (0.00) |
| Blood | 1.79 | 0.24 | 0.05 | 0.74 | 0.18 | 0.04 | 0.77 | 0.23 | 0.04 |
| | (1.03) | (0.10) | (0.01) | (0.18) | (0.05) | (0.01) | (0.06) | (0.01) | (0.01) |

*Taken from Liu, G. et al., J. Nucl. Med. 43:384–391 (2002)...

TABLE 5

Biodistribution of $^{99m}$Tc-MORFs in normal mice (ID %/g, n = 4)

| | MORF15-$^{99m}$Tc | | | MORF18-$^{99m}$Tc | | | MORF25-$^{99m}$Tc | | |
|---|---|---|---|---|---|---|---|---|---|
| Organ | 0.5 h | 1 h | 3 h | 0.5 h | 1 h | 3 h | 0.5 h | 1 h | 3 h |
| Liver | 0.27 | 0.17 | 0.11 | 0.35 | 0.14 | 0.12 | 0.22 | 0.14 | 0.11 |
| | (0.01) | (0.03) | (0.01) | (0.12) | (0.02) | (0.05) | (0.04) | (0.02) | (0.01) |
| Heart | 0.28 | 0.08 | 0.03 | 0.33 | 0.10 | 0.04 | 0.24 | 0.10 | 0.04 |
| | (0.04) | (0.01) | (0.00) | (0.05) | (0.01) | (0.00) | (0.09) | (0.02) | (0.00) |
| Kidney | 9.83 | 7.28 | 7.00 | 10.75 | 8.73 | 7.76 | 11.91 | 11.33 | 9.22 |
| | (2.85) | (1.57) | (0.55) | (2.95) | (0.98) | (1.33) | (5.27) | (1.86) | (1.60) |
| Lung | 0.58 | 0.20 | 0.07 | 0.73 | 0.21 | 0.10 | 0.52 | 0.22 | 0.08 |
| | (0.05) | (0.04) | (0.01) | (0.02) | (0.05) | (0.03) | (0.16) | (0.07) | (0.02) |
| Spleen | 0.29 | 0.10 | 0.09 | 0.21 | 0.10 | 0.08 | 0.21 | 0.11 | 0.07 |
| | (0.12) | (0.01) | (0.06) | (0.03) | (0.02) | (0.05) | (0.08) | (0.01) | (0.01) |
| Muscle | 0.20 | 0.05 | 0.03 | 0.29 | 0.07 | 0.03 | 0.21 | 0.06 | 0.02 |
| | (0.04) | (0.00) | (0.01) | (0.06) | (0.01) | (0.03) | (0.05) | (0.02) | (0.00) |
| Blood | 0.91 | 0.20 | 0.04 | 1.04 | 0.25 | 0.04 | 0.71 | 0.22 | 0.03 |
| | (0.17) | (0.01) | (0.00) | (0.08) | (0.04) | (0.01) | (0.22) | (0.04) | (0.00) | between these two pretargeting studies performed simultaneously should not have influenced these observations.

TABLE 6

Biodistributions of Radiolabeled-cMORF15 or cMORF18 at 3 Hr in Tumor-Bearing Mice

| Organ | 15 mer control | | | 15 mer pretargeting | | | 18 mer pretargeting | | |
|---|---|---|---|---|---|---|---|---|---|
| | ID % | SD | T/NT | ID % | SD | T/NT | ID % | SD | T/NT |
| Liver | 0.18 | 0.08 | 0.86 | 0.44 | 0.02 | 3.1 | 0.51 | 0.12 | 2.4 |
| Heart | 0.00 | 0.00 | 3 | 0.01 | 0.00 | 9.2 | 0.02 | 0.00 | 5.6 |
| Kidney | 1.52 | 0.43 | 0.04 | 1.84 | 0.17 | 0.22 | 3.12 | 0.56 | 0.12 |
| Lung | 0.01 | 0.00 | 1.5 | 0.03 | 0.00 | 4.8 | 0.05 | 0.01 | 3.3 |
| Spleen | 0.01 | 0.01 | 1.5 | 0.02 | 0.00 | 5.8 | 0.03 | 0.00 | 3.0 |
| Stomach | 0.09 | 0.04 | — | 0.23 | 0.06 | — | 0.27 | 0.04 | — |
| Sm. Int. | 0.76 | 0.42 | — | 0.30 | 0.06 | — | 0.23 | 0.04 | — |
| Lg. Int. | 1.30 | 0.43 | — | 0.55 | 0.06 | — | 0.36 | 0.03 | — |
| Muscle | 0.01 | 0.00 | 3 | 0.02 | 0.00 | 12 | 0.02 | 0.01 | 8.8 |
| Tumor | 0.16 | 0.03 | 1.0 | 1.35 | 0.30 | 1.0 | 1.24 | 0.16 | 1.0 |
| Blood | 0.08 | 0.02 | 2 | 0.91 | 0.15 | 1.5 | 1.13 | 0.33 | 1.4 |
| Whole body | 9.4 | 1.3 | — | 10.1 | 1.6 | — | 11.5 | 2.1 | — |

Control animals received $^{99m}$Tc-cMORF15 only, 15 mer pretargeting animals received MN14-MORF15 followed by $^{99m}$Tc-cMORF15, 18 mer pretargeting animals received MN14-MORF18 followed by $^{99m}$Tc-cMORF18 ((ID %/organ, n = 4)

Imaging Study of LSI 74T Tumor-Bearing Nude Mice

Figure 8:
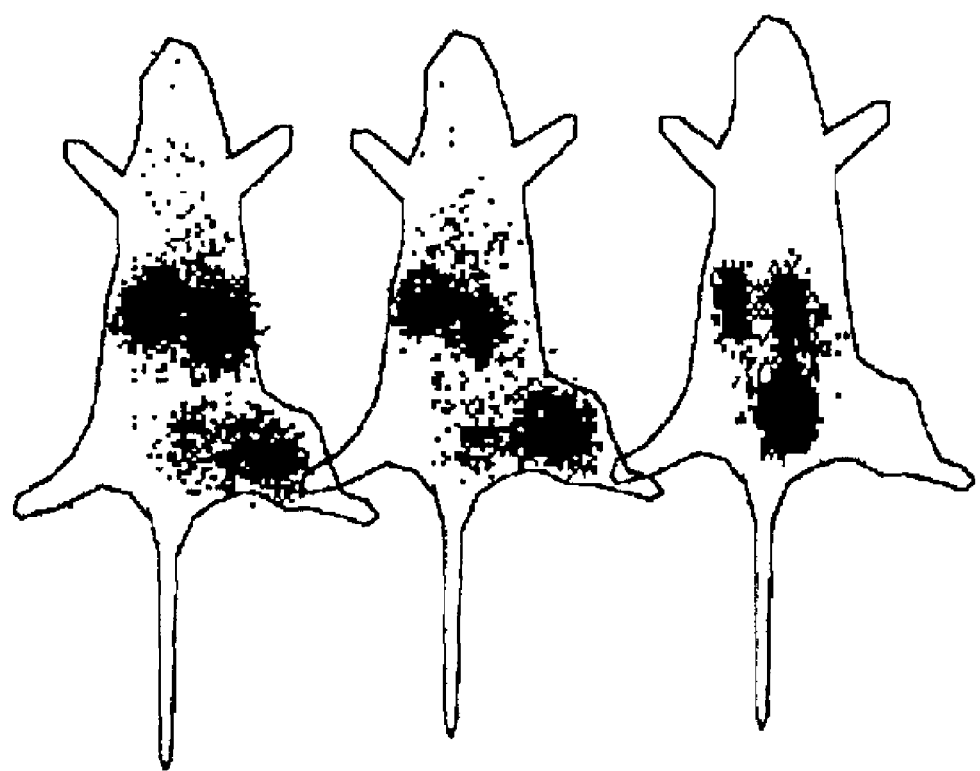
FIG. 8. Whole body scintigraphic images obtained simultaneously of LS174T tumored nude mice at 3 hrs post injection. Control animal received $^{99m}$Tc-cMORF15 only (right image), 15 mer pretargeting animal received MN14-MORF15 followed by $^{99m}$Tc-cMORF15 (middle image) and 18 mer pretargeting animals received MN14-MORF18 followed by $^{99m}$-cMORF18 (left image). Tumors are in the right thigh in each case.

FIG. 8 presents representative whole body images obtained of both a MN14-MORF15 and a MN14-MORF18 pretargeted tumored mouse at 3 hrs post-injection of $^{99m}$Tc-cMORF15 and $^{99m}$Tc-cMORF18 respectively. Both animals and the control were imaged simultaneously. The lower kidney radioactivity levels in the case of the cMORF15-$^{99m}$Tc pretargeted animal compared to the cMORF18-$^{99m}$Tc pretargeted animal provides an obvious improvement to the image.

It will be apparent to those skilled in the art that various modifications and variations can be made to the products, compositions, methods. and processes of this invention. Thus, it is intended that the present invention cover such modifications and variations, provided they come within the scope of the appended claims and their equivalents. The disclosure of all publications cited above are expressly incorporated herein by reference in their entireties to the same extent as if each were incorporated by reference individually.

$^{99m}$TC-Labeled Morpholino Pretargeting in Mice—
a Comparison with Conventional Tumor Targeting Methods: In this study, an anti-CEA antibody (MN-14, Immunomedics) was conjugated with an 18-mer Morpholino (MORF) and with DTPA for labeling with $^{111}$In. Trial conjugations were shown to provide an immunoreactive antibody. Non-specific IgG (Sandoz) wa also conjugated with MORF in the identical fashion as control. In a comparison of pretargeting and conventional targeting, 1, 24, 48, and 72 hrs post IV administration of 15 µg of $^{111}$In-MORF-MN-14 (2 µCi) to LS174-tumor bearing nude mice, 0.15 µg (90 µCi) of the complementary MORF (cMORF) was administered radiolabeled with $^{99m}$Tc via MAG$_3$. The radiolabeled cMORF was also administerred 48 hrs post IV administration of 15, 50 or 100 µg of unlabeled MORF-MN-14 or 50 µg of unlabeled MORF-Sandoz to the tumored animals. Animals were sacrificed sacrifice at 3 hrs following $^{99m}$Tc-cMORF administration and tissues were counted for both radionuclides.

Results: In ID %, tumor uptake was higher at all time points for MN-14 itself vs. labeled cMORF (8–10 vs 1.3–2.3 respectively) due to the rapid clearance of cMORF through the kidneys, however, tumor/normal tissue ratios were superior for pretargeting at all time points and in all tissue except blood (e.g., for 50 µg of antibody, liver: 3 vs. 0.5; muscle: 6–12 vs 5–6; spleen: 2–7 vs 1). These values for blood were 1–3 for pretargeting vs. 1–6 for conventional targeting. By pretargeting alone, these ratios were highest in all tissues for 15 µg compared to higher MN14 dosages but in all cases were superior to that of the Sandoz control. Whole body images of $^{99m}$Tc reflected these trends. The superior tumor/normal tissues ratios for pretargeting can be partially explained through calculations based on both radiolabels. After 24 hrs, the MORF on MN14 was completely bound by $^{99m}$Tc-cMORF in blood but only 5–10% bound in liver and spleen suggesting that the antibody is partially sequestered in these organs. Fortunately, this was not the case in tumor as 50% was bound.

Conclusion: The advantages of pretargeting over conventional targeting were evident in the superior target/nontarget ratios and in the superior images obtained through the use of MORF conjugated anti-tumor antibody and radiolabeled cMORF.

Initial Investigations of $^{99m}$TC-Labeled Morpholino Oligomers for Radiopharmaceutical Applications Methods: Both 15-mer and 18-mer MORFs were purchased, each with a primary amine attached to the 3' equivalent end via a six-member alkyl linker. The amine was used to conjugate with NHS-MAG$_3$ for $^{99m}$Tc radiolabeling.

Results: By surface plasmon resonance at room temperature, the association rate constant for hybridization of the 18-mer MORF to its complementary oligomer (cMORF) was equivalent to that of DNAs and PNAs of comparable length. Hybridization of $^{99m}$Tc-MORF in vitro to free cMORF, to a cMORF polymer and to CMORF beads was nearly quantitative under a variety of conditions. Kinetic studies in vitro at room temperature showed rapid (2–3 min) and nearly quantitative (90%) binding to cMORF beads. Using SE HPLC, the stability of the $^{99m}$Tc-MORF was found to be greater than 85% over 24 hrs in 37° C. serum with minimal protein binding. In normal mice, the $^{99m}$Tc-MORF showed rapid pharmacokinetics with 21% and 8% remaining in the whole body at 3 hrs and 24 hrs post administration, respectively. In vivo targeting with $^{99m}$Tc-MORF of cMORF beads in one thigh of normal mice compared to native streptavidin beads in the other (control) thigh showed ratios of 4–7 between 3–24 hrs for study/control thigh.

Conclusions: Our results demonstrate that MORF oligomers are capable of in vivo hybridization. Their properties of hybridization affinity and kinetics and their in vivo stability and pharmacokinetics make them suitable for in vivo studies.

What we claim is:

1. A kit for targeting of a diagnostic or therapeutic agent to a target site comprising:
    (a) a first conjugate comprising a targeting moiety and a Morpholino oligomer, wherein said targeting moiety binds selectively to a primary, target-specific binding site of the target site or to a substance produced by or associated with the target site;
    (b) optionally, a clearing agent; and
    (c) a second conjugate comprising a complementary Morpholino oligomer and a diagnostic agent or therapeutic agent.

2. The kit of claim 1, wherein said targeting moiety comprises a humanized antibody or an antigen-binding fragment of a humanized antibody.

3. The kit of claim 2, wherein said humanized antibody is an anti-carcinoembryonic antigen (CEA) antibody.

4. The kit of claim 1, wherein said targeting moiety is selected from the group consisting of proteins, small peptides, polypeptides, enzymes, hormones, steroids, cytokines, neurotransmitters, oligomers, vitamins and receptor binding molecules.

5. The kit of claim 1, wherein the length of said Morpholino oligomer is at least about 6 bases to about 100 bases.

6. The kit of claim 1, wherein the length of said complementary Morpholino oligomer is at least about 6 bases to about 100 bases.

7. The kit of claim 1, wherein said Morpholino oligomer is 15-mer, 18-mer or 25-mer.

8. The kit of claim 1, wherein said target moiety is bound to a 15-mer Morpholino oligomer.

9. The kit of claim 1, wherein said target moiety is bound to an 18-mer Morpholino oligomer.

10. The kit of claim 1, wherein said target moiety is bound to a 25-mer Morpholino oligomer.

11. The kit of claim 1, wherein said complementary Morpholino oligomer is 15-mer, 18-mer or 25-mer.

12. The kit of claim 1, wherein said clearing agent is an anti-idiotypic antibody or antigen-binding antibody fragment.

13. The kit of claim 1, wherein said therapeutic agent is selected from the group consisting of antibodies, antibody fragments, drugs, toxins, nucleases, hormones, immunomodulators, chelators, boron compounds, photoactive agents or dyes and radioinuclides.

14. The kit of claim 13, wherein said chelator is selected from the group consisting of hydrazino nicotinamide (HYNIC), diethylenetriaminepentaacetic acid (DTPA), 1, 4, 7, 10-tetraazacyclododecane N, N', N", N'''-tetraacetic acid (DOTA), and mercaptoacetylglycylgly-cylglycine ($MAG_3$).

15. The kit of claim 13, wherein said radionuclide substantially decays by beta-particle emission and is selected from the group consisting of P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213.

16. The kit of claim 15, wherein said radionuclide has a maximum decay energy of 20–5,000 keV.

17. The kit of claim 15, wherein said radionuclide has a maximum decay energy of 100–4,000 keV.

18. The kit of claim 15, wherein said radionuclide has a maximum decay energy of 500–2,500 keV.

19. The kit of claim 13, wherein said radionuclide substantially decays by Auger particle emission and is selected from the group consisting of Co-58, Ga-67, Br-80m, Tc-99m, Rh-103m, Pt-109, In-111, Sb-119, I-125, Ho-161, Os-189m and Ir-192.

20. The kit of claim 19, wherein said radionuclide has a maximum decay energy of less than 1,000 keV.

21. The kit of claim 19, wherein said radionuclide has a maximum decay energy of less than 100 keV.

22. The kit of claim 19, wherein said radionuclide has a maximum decay energy of less than 70 keV.

23. The kit of claim 13, wherein said radionuclide substantially decays by alpha-particle emission and is selected from the group consisting of Dy-152, At-211, Bi-212, Ra-223, Rn-219, Po-215, Bi-211, Ac-225, Fr-221, At-217, Bi-213 and Fm-255.

24. The kit of claim 23, wherein said radionuclide has a maximum decay energy of 2,000–9,000 keV.

25. The kit of claim 23, wherein said radionuclide has a maximum decay energy of 3,000–8,000 keV.

26. The kit of claim 23, wherein said radionuclide has a maximum decay energy of 4,000–7,000 keV.

27. The kit of claim 1, wherein said therapeutic agent is used in photodynamic therapy and neutron capture procedures.

28. The kit of claim 27, wherein said photodynamic therapy uses metal complexes, and said metal complexes are selected from the group consisting of zinc, aluminum, gallium, lutetium and palladium.

29. The kit of claim 27, wherein said neutron capture procedures uses a radionuclide selected from the group consisting of B-10, Gd-157 and U-235.

30. The kit of claim 1, wherein said diagnostic agent is selected from the group consisting of radionuclides, dyes, contrast agents, fluorescent compounds or molecules and enhancing agents useful for magnetic resonance imaging (MRI).

31. The kit of claim 30, wherein said diagnostic agent is a radionuclide useful in positron emission and said radionuclide is selected from the group consisting of F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124.

32. The kit of claim 31, wherein said radionuclide has a maximum decay energy of less than 2,000 keV.

33. The kit of claim 31, wherein said radionuclide has a maximum decay energy of less than 1,000 keV.

34. The kit of claim 31, wherein said radionuclide has a maximum decay energy of less than 700 keV.

35. The kit of claim 30, wherein said diagnostic agent is useful in magnetic resonance imaging techniques and wherein said magnetic resonance imaging techniques use metals that are selected from the group consisting of gadolinium, manganese, iron, chromium, copper, cobalt, nickel, dysprosium, rhenium, europium, terbium, holmium and neodymium.

36. The kit of claim 30, wherein said diagnostic agent is a radionuclide useful in gamma-ray detection and wherein said radionuclide is selected from the group consisting of Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201.

37. The kit of claim 36, wherein said radionuclide has a maximum decay of 20–2000 keV.

38. The kit of claim 36, wherein said radionuclide has a maximum decay of 60–600 keV.

39. The kit of claim 36, wherein said radionuclide has a maximum decay of 100–300 keV.

40. A targeting method for delivering a diagnostic or therapeutic agent to a target site in a mammal, comprising:
  (a) administering to said mammal a first conjugate comprising a targeting moiety and a Morpholino oligomer, wherein said targeting moiety binds selectively binds to a primary, target-specific binding site of the target site or to a substance produced by or associated with the target site;
  (b) optionally, administering to said mammal a clearing agent, and allowing said clearing agent to clear non-localized first conjugate from circulation; and
  (c) administering to said mammal a second conjugate comprising a complementary Morpholino oligomer and a diagnostic agent or therapeutic agent, wherein said complementary Morpholino oligomer binds to its Morpholino oligomer complement on the first conjugate, thereby targeting the diagnostic agent or therapeutic agent to the target site.

41. The targeting method of claim 40, said diagnostic agent or therapeutic agent is administered intravenously, intraarterially, intrapleuraly, intraperitoneally, intrathecally, subcutaneously or by perfusion.

42. The targeting method of claim 40, wherein said method is used for internal detection or treatment of tumors or other lesions, infectious diseases, inflammatory diseases, and autoimmune diseases.

43. The targeting method of claim 40, wherein said method is used in conjunction with intraoperative probes, endoscopic and laparoscopic uses, and in methods for imaging normal organs.

44. The kit of claim 2, wherein said humanized antibody is administered at a dosage range of from 15 micrograms to 100 micrograms.

45. The kit of claim 2, wherein said humanized antibody is administered at a dose of 15 micrograms.

46. The kit of claim 2, wherein said humanized antibody is administered at a dose of 50 micrograms.

47. The kit of claim 3, wherein said anti-carcinoembryogenic antigen antibody is an anti-MN14 antibody.

\* \* \* \* \*